United States Patent
Sand

(10) Patent No.: US 7,278,778 B2
(45) Date of Patent: Oct. 9, 2007

(54) SYSTEM FOR MIXING AND TRANSFERRING FLOWABLE MATERIALS

(75) Inventor: Paul M Sand, San Carlos, CA (US)

(73) Assignee: Kyphon Inc., Sunnyvale, CA (US)

( * ) Notice: Subject to any disclaimer, the term of this patent is extended or adjusted under 35 U.S.C. 154(b) by 0 days.

(21) Appl. No.: 11/651,164

(22) Filed: Jan. 9, 2007

(65) Prior Publication Data

US 2007/0121422 A1    May 31, 2007

Related U.S. Application Data

(62) Division of application No. 11/409,776, filed on Apr. 24, 2006, now Pat. No. 7,160,020, which is a division of application No. 09/980,648, filed on Oct. 25, 2001, now abandoned.

(60) Provisional application No. 60/243,195, filed on Oct. 25, 2000.

(51) Int. Cl.
*B01F 13/06* (2006.01)
(52) U.S. Cl. ................. 366/139; 366/189
(58) Field of Classification Search ............ 366/139, 366/189, 142, 242–252, 255–256, 267, 288, 366/333; 248/94
See application file for complete search history.

(56) References Cited

U.S. PATENT DOCUMENTS

| | | |
|---|---|---|
| 1,310,861 A | 7/1919 | Fowler |
| 2,372,872 A | 4/1945 | Wolper |
| 2,453,914 A | 11/1948 | Hollenback |
| 2,696,022 A | 12/1954 | Steinbock et al. |
| 3,164,303 A | 1/1965 | Trautmann |
| 3,195,778 A | 7/1965 | Coates |
| 3,343,817 A | 9/1967 | Carangelo et al. |
| 3,358,971 A | 12/1967 | Steinbock, Jr. |
| 3,546,129 A | 12/1970 | Youngdahl |
| 3,640,510 A | 2/1972 | Lea |
| 4,185,072 A | 1/1980 | Puderbaugh et al. |
| 4,277,184 A | 7/1981 | Solomon |
| 4,294,293 A | 10/1981 | Lorenz et al. |
| D279,499 S | 7/1985 | Case |
| 4,671,263 A | 6/1987 | Draenert |
| 4,721,390 A | 1/1988 | Lidgren |
| 4,758,096 A | 7/1988 | Gunnarsson |
| 4,776,704 A | 10/1988 | Kopunek et al. |
| 4,961,647 A | 10/1990 | Coutts et al. |
| 4,973,168 A | 11/1990 | Chan |
| 5,215,536 A | 6/1993 | Lampropoulos et al. |
| 5,348,391 A | 9/1994 | Murray |
| 5,368,386 A | 11/1994 | Murray |

(Continued)

FOREIGN PATENT DOCUMENTS

| | | |
|---|---|---|
| DE | 299 22 445 | 4/2000 |
| WO | 86/06618 | 11/1986 |
| WO | 96/40424 | 12/1996 |
| WO | 97/21485 | 6/1997 |
| WO | 99/37256 | 7/1999 |
| WO | 99/67015 | 12/1999 |

*Primary Examiner*—Charles E. Cooley
(74) *Attorney, Agent, or Firm*—Ryan Kromholz & Manion, S.C.

(57) ABSTRACT

A plurality of bone filler devices receive bone filling material from an apparatus that receives components of the bone filling material in an unmixed condition, mixes the components of the bone filling material, and dispenses the mixed components of the bone filling material through a fitting into each of the plurality of bone filler devices, all while a base supports the apparatus in an upright condition.

6 Claims, 22 Drawing Sheets

U.S. PATENT DOCUMENTS

| | | |
|---|---|---|
| 5,415,474 A | 5/1995 | Nelson et al. |
| 5,494,349 A | 2/1996 | Seddon |
| 5,501,371 A | 3/1996 | Schwartz-Feldman |
| 5,549,381 A | 8/1996 | Hays et al. |
| 5,588,745 A | 12/1996 | Tanaka et al. |
| 5,624,184 A | 4/1997 | Chan |
| D381,084 S | 7/1997 | Vish |
| 5,794,904 A | 8/1998 | Hackley |
| 5,797,678 A | 8/1998 | Murray |
| 5,797,679 A | 8/1998 | Grulke et al. |
| 5,842,785 A | 12/1998 | Brown et al. |
| 5,842,786 A | 12/1998 | Solomon |
| 5,876,116 A | 3/1999 | Barker et al. |
| 5,934,803 A | 8/1999 | Hutter |
| 5,938,644 A | 8/1999 | Kirk |
| 5,951,160 A | 9/1999 | Ronk |
| 5,961,211 A | 10/1999 | Barker et al. |
| 5,975,751 A | 11/1999 | Earle |
| 6,024,480 A | 2/2000 | Seaton et al. |
| 6,033,105 A | 3/2000 | Barker |
| 6,042,262 A | 3/2000 | Hajianpour |
| 6,116,773 A | 9/2000 | Murray |
| 6,120,174 A | 9/2000 | Hoag et al. |
| 6,176,607 B1 | 1/2001 | Hajianpour |
| D472,323 S | 3/2003 | Sand |
| 6,536,937 B1 | 3/2003 | Burchett |
| 6,592,247 B1 | 7/2003 | Brown et al. |
| D483,495 S | 12/2003 | Sand |
| D490,159 S | 5/2004 | Sand |
| 7,160,020 B2 * | 1/2007 | Sand .................... 366/139 |
| 2002/0191487 A1 | 12/2002 | Sand |
| 2006/0133193 A1 | 6/2006 | Arramon |

* cited by examiner

SYSTEM FOR MIXING AND TRANSFERRING FLOWABLE MATERIALS

RELATED APPLICATION

This application is a divisional of U.S. patent application Ser. No. 11/409,776, filed Apr. 24, 2006 (now U.S. Pat. No. 7,160,020), and entitled "Systems and Methods for Mixing and Transferring Flowable Materials," which is a divisional of U.S. patent application Ser. No. 09/980,648, filed Oct. 25, 2001 and entitled "Systems and Methods for Mixing and Transferring Flowable Materials" (now abandoned), which claims the benefit of U.S. provisional application Ser. No. 60/243,195 filed 25 Oct. 2000.

FIELD OF THE INVENTION

The invention relates to systems and methods for mixing materials together and transferring the materials into other instruments, particularly for use in the medical field.

BACKGROUND OF THE INVENTION

Current methods and apparatus for mixing a plurality of materials together in the medical field, e.g., poly(methyl methacrylate) bone cement comprising a powdered material with a liquid monomer to be used as a bone filling material, often yield unsatisfactory results.

Typically, in a surgical setting, the instruments employed for this purpose are a small bowl for receiving the components and a stick (such as a common tongue depressor) for mixing the components in the bowl. If a powdered material is employed, it is usually poured directly from its container into the bowl. Consequently, the process is often messy due to spillage of the powdered material. Where one of the components is a liquid monomer, the process can involve the release of noxious fumes released by the liquid monomer.

After the components are mixed, as in the case of a bone filling material, further problems are encountered. When the bone filling material is to be dispensed into a cavity in bone, the common practice is to first transfer the material into a syringe and then to transfer the material into the instrument for delivery to the cavity. The syringe is loaded by either vacuuming up the material by withdrawing the fully engaged plunger through the syringe body, or by removing the syringe plunger and pouring the material into the back of the syringe and reinserting the plunger. This is a difficult and messy procedure. Thus, there is a need for providing a way of mixing materials while containing the fumes and to easily and cleanly transfer or dispense the contents into other instruments.

SUMMARY OF THE INVENTION

Although various manufacturers of medical products have attempted to develop, manufacture and supply various systems for mixing and/or dispensing poly(methyl methacrylate) bone cement (e.g., DePuy—see PCT Publication No. WO97/21485, Immedica—see PCT Publication No. WO99/37256, and Stryker—see U.S. Pat. No. 6,042,262) such systems are often expensive, too complex, require extensive and/or externally-powered accessories, or cannot mix small quantities of bone filler material. Because of these and other problems, there is a need for improved systems and methods for mixing and transferring materials, particularly in the medical field.

One aspect of the invention provides a system that comprises a plurality of bone filler devices and an apparatus for dispensing bone filling material into the bone filler devices. The apparatus receives unmixed components of the bone filler material, mixes the components of the bone filling material, and dispenses the mixed bone filler material through a fitting into each of the plurality of bone filler devices, all while a base supports the apparatus in an upright condition.

DETAILED DESCRIPTION OF THE EMBODIMENTS

The embodiments describe systems and methods that embody features of the invention in the context of mixing a bone filling material. It should be appreciated, however, that the systems and methods so described are not limited in their application to the mixing of bone filling material. The systems and methods are applicable for use in diverse applications, both inside and outside the medical field.

It should also be appreciated that the various component parts of the inventions described herein can be comprised of non-ferrous and/or non-metallic materials, which would permit the various embodiments to be utilized in a magnetic and/or whole room MRI environment.

I. The Component Parts

Figure 1A:
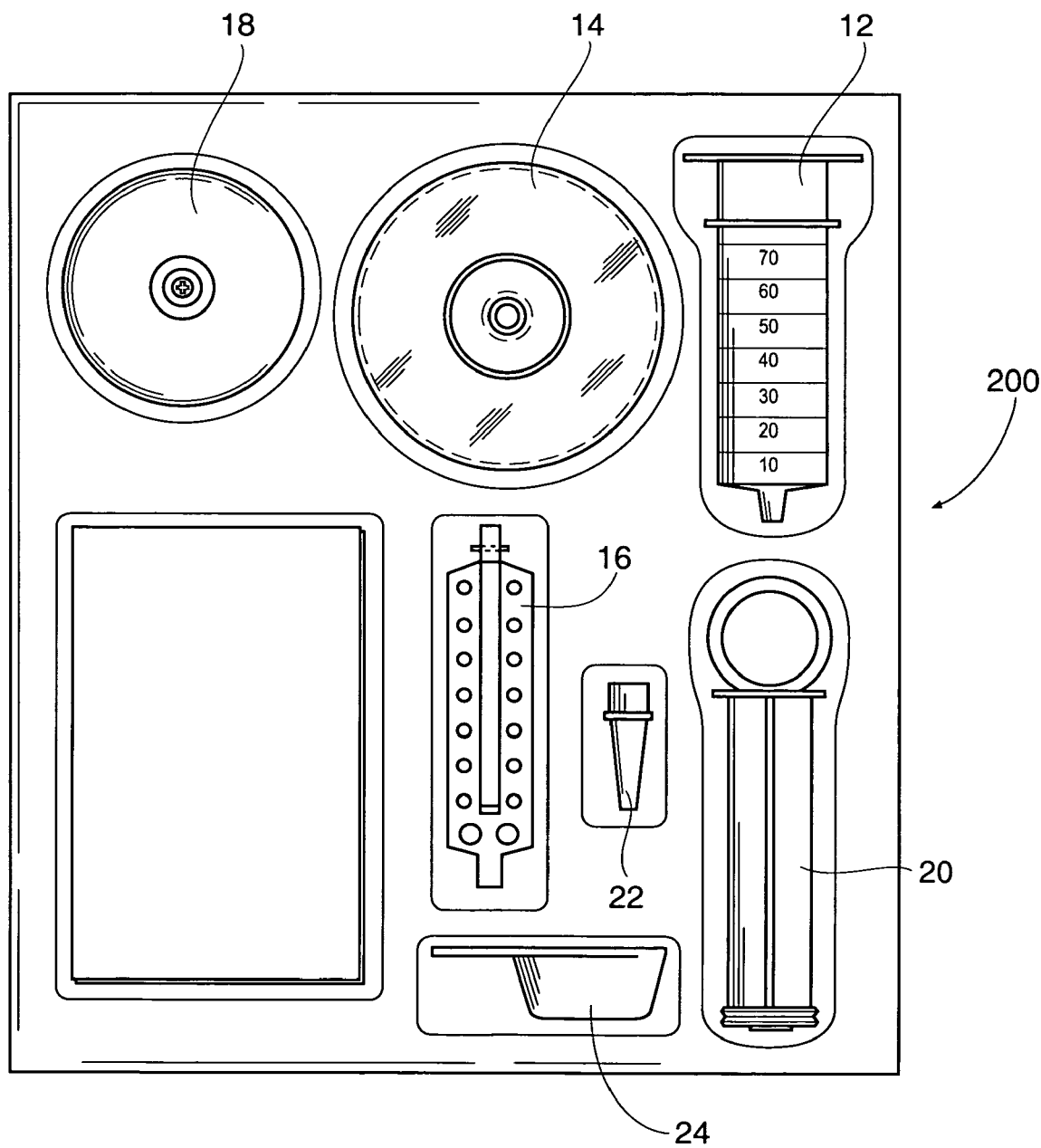
FIGS. 1A and 1B are plane views of various embodiments of a kit that contains the component parts of systems for mixing and dispensing flowable materials that embody features of the invention.

FIG. 1A shows component parts, arranged as a kit 200, that are usable in association with each other to form a material mixing and transferring system. The number and structure of the component parts can vary. In FIG. 1A, the kit 200 includes a receptacle 12 for receiving materials for mixing and for, after mixing, transferring or dispensing the materials a stand 14 for receiving the receptable 12; a mixing element 16 that can be inserted into the receptacle 12 to mix the materials; an actuator 18 to drive the mixing element 16; a plunger 20 that can be inserted into the receptacle 12 to urge mixed materials from the receptacle 12; a dispensing element 22 to dispense the mixed materials urged from the receptacle 12; and a measuring device 24 to measure materials placed in the receptacle 12 for mixing.

Desirably, the components 12, 14, 16, 18, 20, 22 and 24 comprise a substantially rigid metal, plastic or ceramic material. In one embodiment, the components 12, 14, 16, 20, 22 and 24 comprise polypropylene, and component 18 comprises Acetal homopolymer (DELRIN®) material from DuPont Corporation) or a clear or colored nylon. The component materials will desirably be unaffected by contact with the bone filler material and/or sterilizable by gamma radiation. Of course, various other alternative materials can be used, including materials which are capable of withstanding contact with monomer without significant degradation for limited periods of time.

A. The Receptacle

Figure 2A:
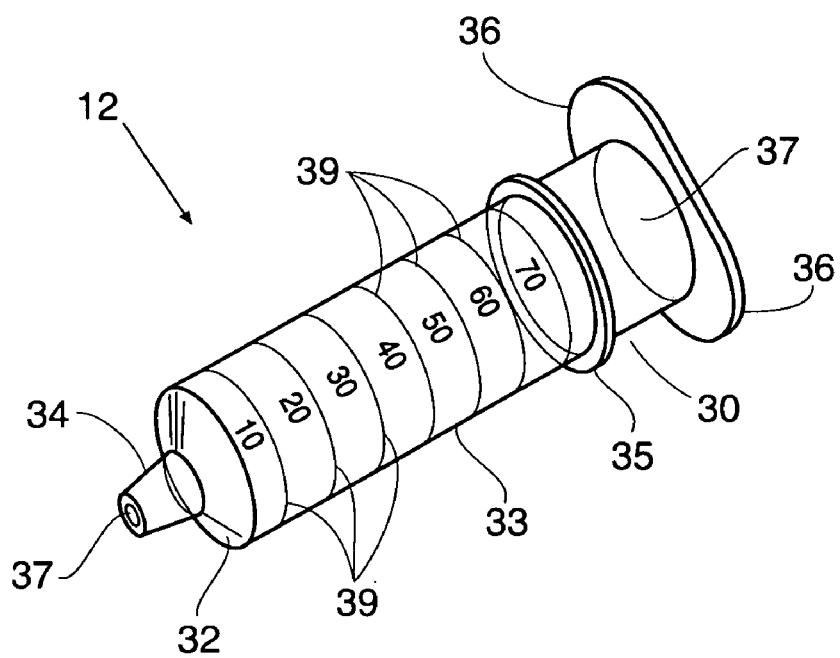
FIGS. 2A and 2B are perspective views of various embodiments of receptacles that form a part of the system shown in FIGS. 1A and 1B.

As shown in FIG. 2A, the receptacle 12 has a proximal end 30 and a distal end 32. The receptacle 12 further has an interior bore 37 which desirably extends from the proximal end 30 to the distal end 32. The distal end 32 carries a distal tip 34, through which one may dispense a material such as a bone filling material.

The receptacle 12 is sized to separately accommodate the mixing element 16 and the plunger 20 at different stages of use. The interior surface of the distal tip 34 is sized to support the distal tip 62 of the mixing element 16 during use, as will be described in greater detail later. The proximal end 30 carries a set of tabs 36 on an outer surface 33 of the receptacle 12, to couple the receptacle to the actuator 18, which, in turn, releasably couples to the proximal end 56 of the mixing element 16. When the plunger 20 is inserted into the receptacle 12, the tabs 36 also allow the physician to grasp and operate the receptacle 12 and plunger 20 like a syringe, for dispensing materials after mixing, as will be described later.

In one embodiment, the receptacle 12 has a volume of approximately seventy cubic centimeters (70 cc). Of course, other size receptacles 12 could be used, depending upon the size of the mixing element 16 and other associated components, and the desired amount of filler material to be mixed. Other representative sizes could include five (5), ten (10) and twenty (20) cc syringes. The outer surface 33 of the receptacle 12 desirably includes a graduated scale 39 showing the volume inside the receptacle 12. Preferably, the graduated scale 39 begins near the distal tip 34 of the receptacle 12. The receptacle 12 is desirably made of transparent polypropylene to allow viewing of the materials to be mixed when placed in the receptacle 12, during mixing and during transfer.

Figure 2B:
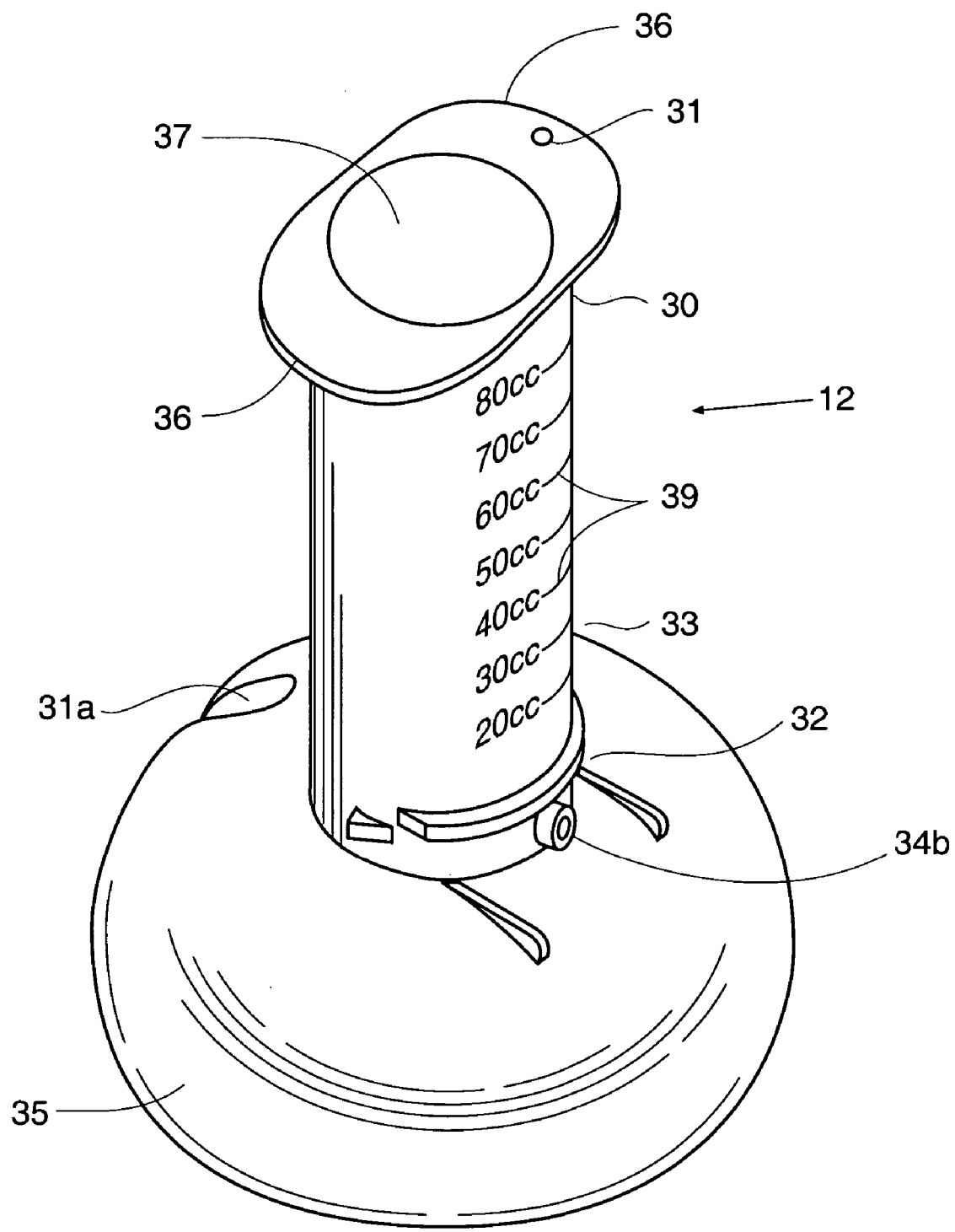

In an alternate embodiment, as shown in FIG. 2B, the receptacle 12 at the distal end 32 comprises a receptacle base 35. The receptacle base 35 is generally hemispherical in shape and supports the interior bore 37 of the receptacle 12. Within the interior bore 37 of the receptacle 12, at the receptacle base 35, is located a central neck (not shown) that is sized to accept and to securely hold the distal tip 62 of the mixing element 16, as previously described in connection with the previous embodiment. The receptacle base 35 desirably stabilizes and elevates the interior bore 37 and allows for easier dispensing or transfer of the mixed material. The receptacle base 35 is sized to provide a solid footing to minimize tipping of the receptacle 12. The receptacle 12 has an outlet 34B for dispensing the mixed bone filling material.

If desired, the receptacle 12 may incorporate a vacuum attachment 31 (see FIG. 2B) for a standard operating room suite vacuum hose, to evacuate fumes in the receptacle 12 and/or degas the material. The vacuum hose may be further secured by an indent 31A in the receptacle base 35. If further desired, the receptacle 12 may form a cartridge for a bone filling material delivery gun.

B. The Stand

Figure 3:
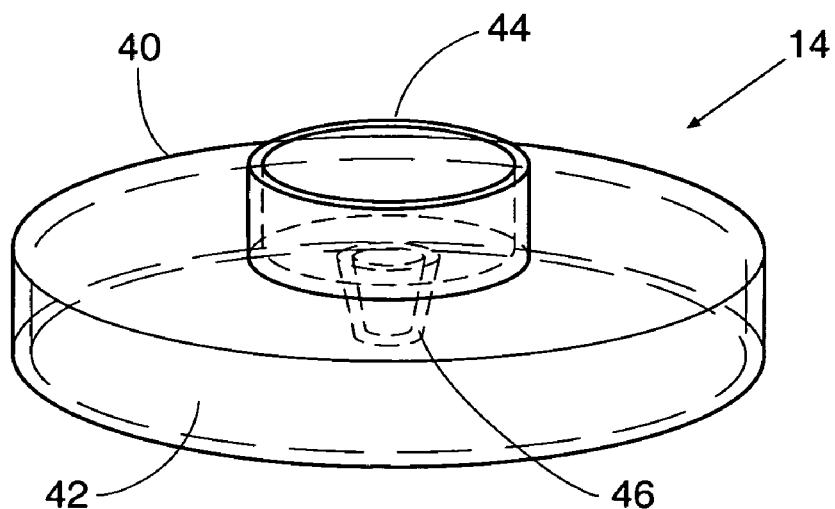
FIG. 3 is a perspective view of a stand that forms a part of the system shown in FIG. 1A.

In the system shown in FIG. 1A, the stand 14 (see FIG. 3) supports the receptacle 12 during mixing. The stand 14 has an upper side 40 and a lower side 42. The upper side 40 has a central neck 44 that is sized to accept and to securely hold the distal end 32 of the receptacle 12. Centered within the neck 44 is a small chamber 46 that is sized to accept the distal tip 34 of the receptacle 12. The lower side 42 of the stand 14 has a flat surface which allows the stand 14 to sit evenly on a surface such as a treatment table.

Figure 1B:
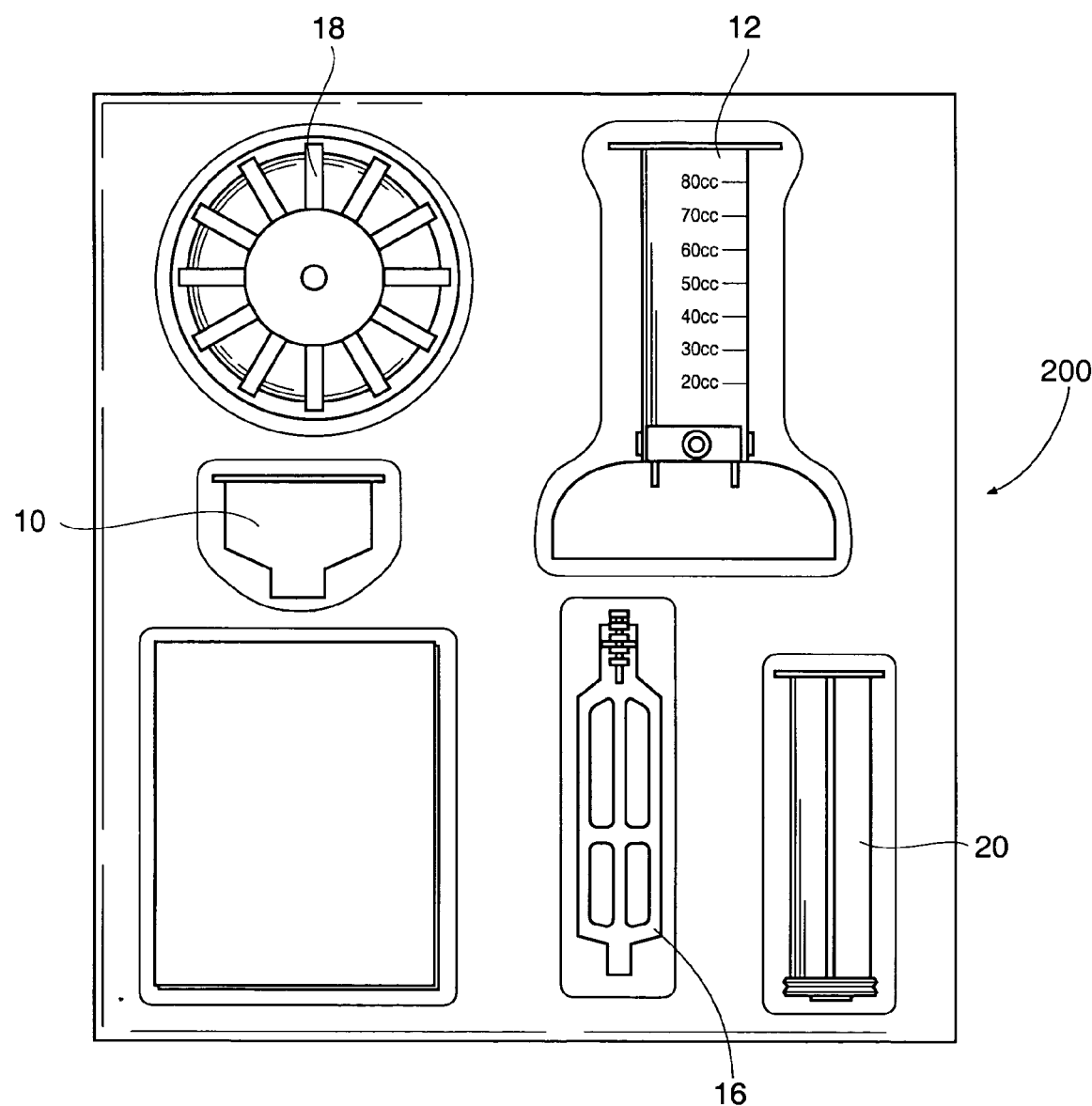

A separate stand 14 is not absolutely necessary for the system shown in FIG. 1B as the receptacle base 35 is incorporated directly into the receptacle 12.

C. The Mixing Element

Figure 7:
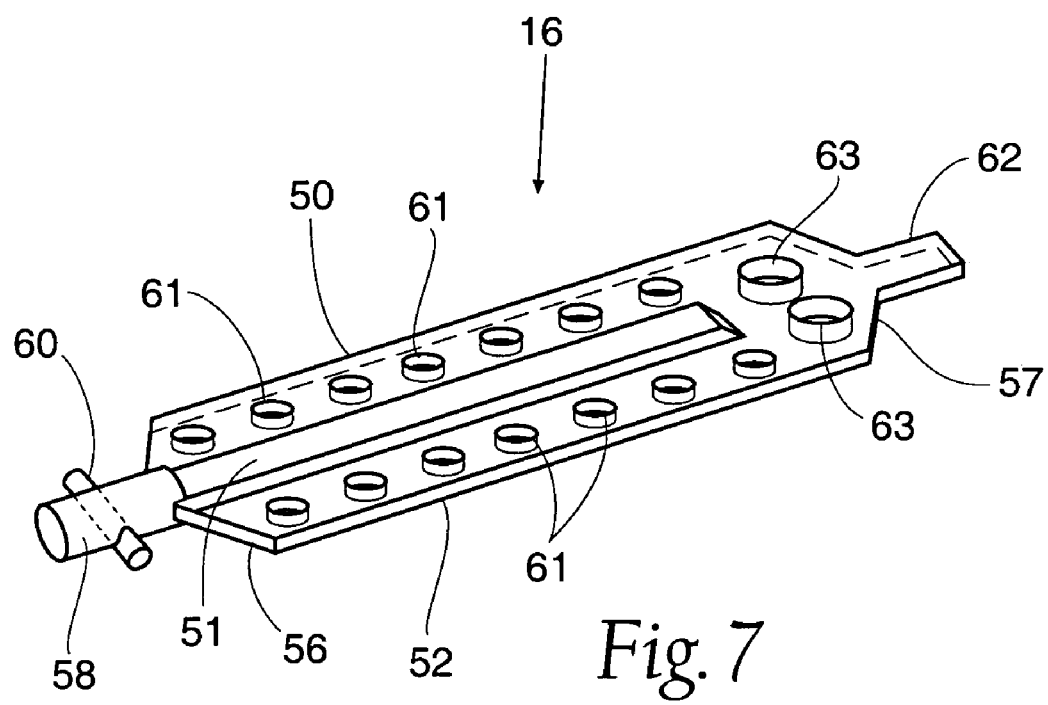
FIG. 7 is a perspective view of one embodiment of a mixing element that forms a part of the system shown in FIGS. 1A and 1B.
Figure 8:
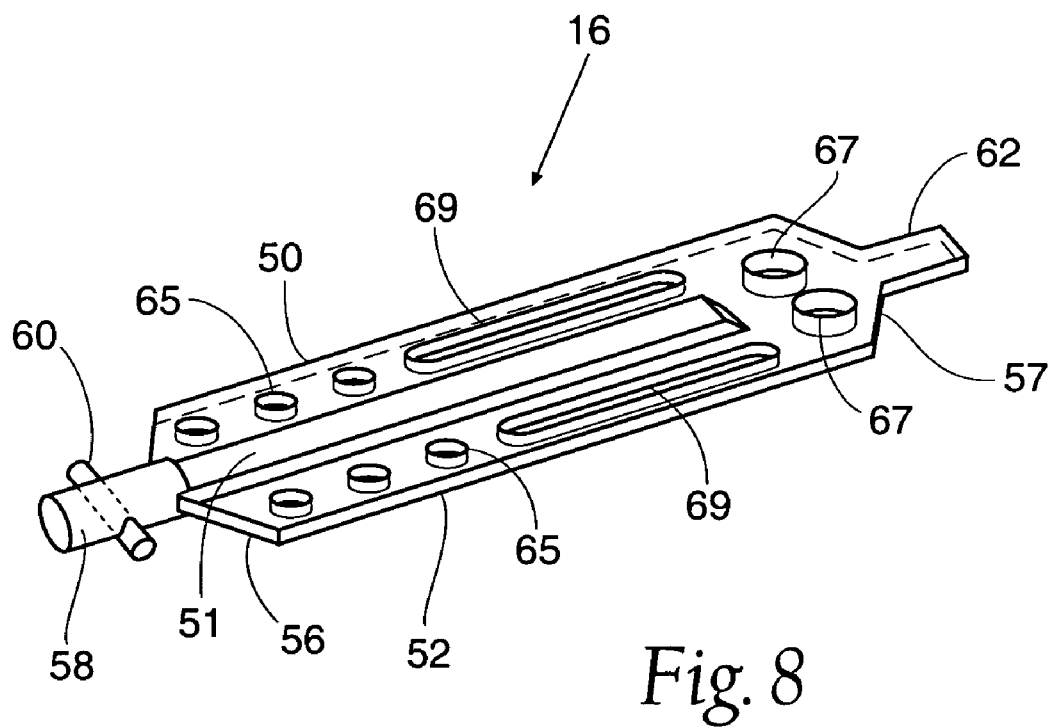
FIG. 8 is a perspective view of another embodiment of the mixing element that forms a part of the system shown in FIGS. 1A and 1B.
Figure 9:
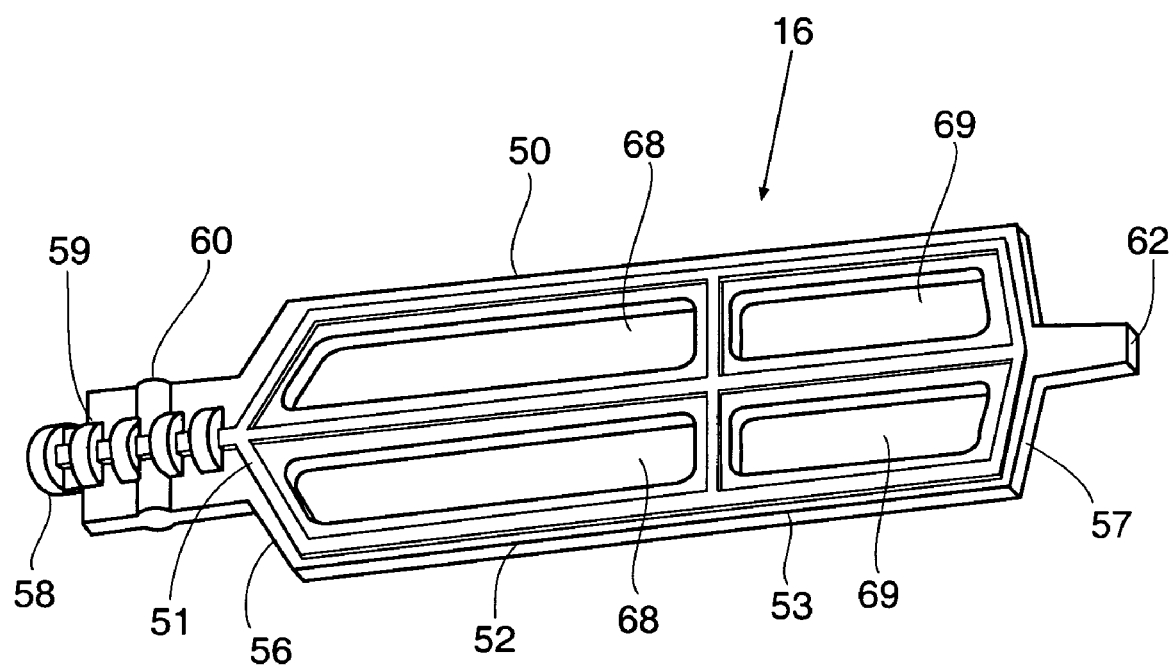
FIG. 9 is a perspective view of another embodiment of the mixing element that forms a part of the system show in FIGS. 1A and 1B.

The mixing element 16 can be variously configured, and FIGS. 7, 8 and 9 show different representative configurations. In use, the mixing element 16 rotates within the receptacle 12 to mix the materials contained in the receptacle.

In the various described configurations, the mixing element 16 has an upper side 50 and a lower side 52. In these embodiments, the upper and lower sides 50 and 52 can have an outwardly extending central rib 51 that acts as a stiffener to maintain integrity of the mixing element 16. The mixing element 16 may also include one or more crosswise ribs 53.

The mixing element 16 has a proximal end 56 and a distal end 57. The distal end 57 desirably carries a flat tip 62 that is adapted to fit into the distal tip 34 of the receptacle 12. The distal tip 62 of the mixing element 16 desirably mixes the components located in the distal tip 34 of the receptacle 12. The distal tip 62 also desirably acts as a bearing surface within the distal tip 34 of the receptacle 12, to keep the mixing element 16 centered within the receptacle 12 as it rotates, as well as constraining side-to-side movement of the mixing element 16 within the receptacle 12. The distal tip 62 also acts to maintain secure engagement of the mixing element 16 to the actuator 18

If desired, the proximal end 56 can carry a solid cylindrical tip 58, although the proximal end 56 could be various configurations suitable for attachment to the actuator 18. The tip 58 is adapted to couple to the actuator 18, as will be described in greater detail later. The tip 58 has a crosspiece 60 that facilitates the transmission of rotational forces from the actuator 18 to the mixing element 16 as shown in FIGS. 7, 8 and 9. The crosspiece 60 also acts to firmly engage the mixing element 16 with the keyway 89 of the actuator 18 by snapping in place. The tip 58 may also contain ridges 59 as shown in FIG. 9 to impart further strength and stability.

The mixing element 16 also desirably has one or more apertures 61, 63, 65, 67, 68, and 69, as shown in FIGS. 7-9. The apertures 61, 63, 65, 67, 68, and 69 function to assist in mixing the chosen components, such as a powdered material and a liquid monomer, together. The apertures 61, 63, 65, 67, 68, and 69 are desirably large enough to allow some of the mixture to flow through the mixing element 16, thereby allowing the mixing element 16 to rotate within the receptacle 12 with a minimum of resistance and maximizing the mixing of the chosen mixing materials. If the sizes of the apertures 61, 63, 65, 67, 68, and 69 are increased, less resistance to rotation is noted. However, there is a concomitant need for additional rotation of the mixing element 16 in the mixture to ensure thorough mixing. Larger apertures ease the mixing process, while smaller apertures may result in the components "riding up" the mixing element 16. In such a case, the mixing must be stopped momentarily in order to allow the components to fall back into the mixture.

Desirably, the mixing element 16 is sized to extend substantially across the interior of the receptacle 12. Such an arrangement can facilitate mixing of the powder and liquid components, because rotation of the mixing element 16 can "scrape" the powdered and liquid components off the inner walls of the receptacle, ensuring even mixing of the components. While actual physical contact between the side walls of the receptacle 12 and the mixing element 16 are not absolutely necessary, in least one embodiment the mixing element 16 and the side walls of the receptacle 12 are in very close proximity.

In the embodiment shown in FIG. 8, the mixing element 16 desirably has a series of small, evenly spaced apertures 65 beginning near the proximal end 56 of the mixing element 16, followed by at least two large apertures 69 extending toward the distal end 57 of the mixing element 16, and at least two intermediate sized apertures 67 at the distal end 57. Such an embodiment allows for easier mixing and minimizes the previously mentioned "riding up" of the mixture; however, this embodiment typically requires additional rotations of the actuator 18. In this embodiment approximately five to twenty rotations of the actuator 18 should be sufficient to ensure a proper mixture in the case of a bone filling material.

In the embodiment shown in FIG. 7, the mixing element 16 has a plurality of evenly spaced apertures 61 that are positioned parallel to the rib 51, and the mixing element 16 further has at least two apertures 63 at the distal tip 62. This embodiment requires approximately five to ten rotations of the actuator 18 to mix a proper bone filling material. Although fewer rotations are needed with this embodiment, this embodiment typically requires more strength for the rotations on behalf of the operator than does the previously mentioned embodiment. Additionally, it is occasionally necessary to stop during the mixing process to allow the components to fall back into the mixture.

In the embodiment shown in FIG. 9, the mixing element 16 has two larger apertures 68 beginning near the proximal end 58 of the mixing element 16, followed by at least two large apertures 69 extending toward the distal end 57. This embodiment requires approximately fifteen to twenty rotations of the actuator 18 to properly mix the bone filling material. The minimal surface area of the mixing element 16 as shown in FIG. 9 allows only a small amount of bone filler material to be retained on the mixing element 16 when it is removed from the receptacle 12 after thorough mixing.

In other alternative embodiments, the mixing element 16 could incorporate any number of apertures of various sizes and shapes (not shown).

D. The Actuator

Figure 4:
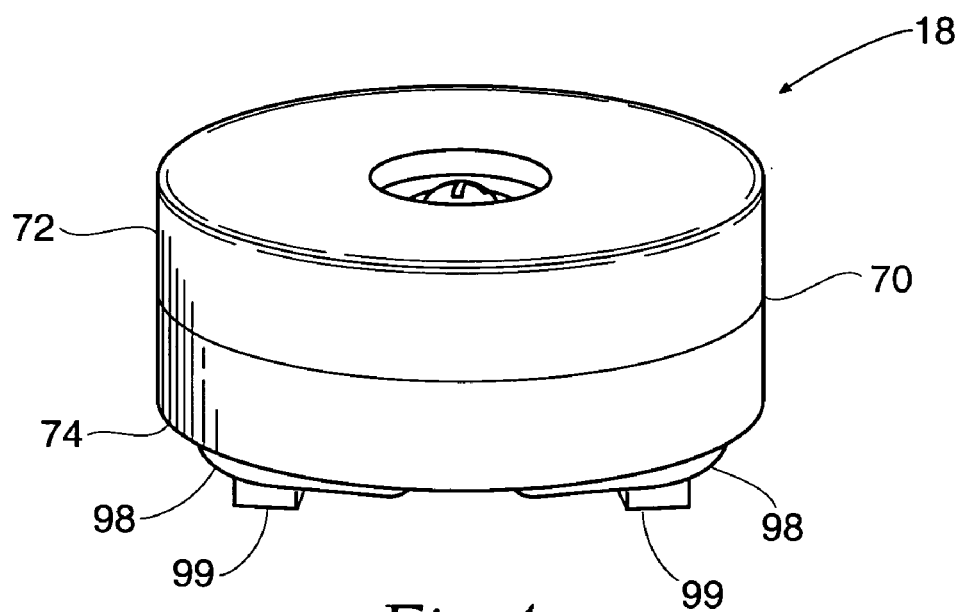
FIG. 4 is perspective side view of an actuator that can form a part of the systems shown in FIGS. 1A and 1B.

The actuator 18 (see FIGS. 4 and 5A and 5B) drives the mixing element 16. Desirably, the actuator 18 is formed from DELRIN☐ material or a clear or colored nylon. As shown in FIG. 4, the actuator 18 is in a palm-sized, cylindrical shape.

The actuator 18 has an outer surface 70 that, if desired, may be knurled or indented to facilitate gripping by the user. FIGS. 4A-4F show various alternative handle designs for an actuator. The actuator 18 has an upper half 72 and a lower half 74 (see also FIGS. 6A and 6B) that are adapted to be connected together in various ways, including fasteners, adhesives, or a snap-fit.

The upper half 72 of the actuator 18 functions as a drive member, while the lower half 74 of the actuator 18 is a driven member. The upper half 72 rotates relative to the lower half 74.

Figure 6A:
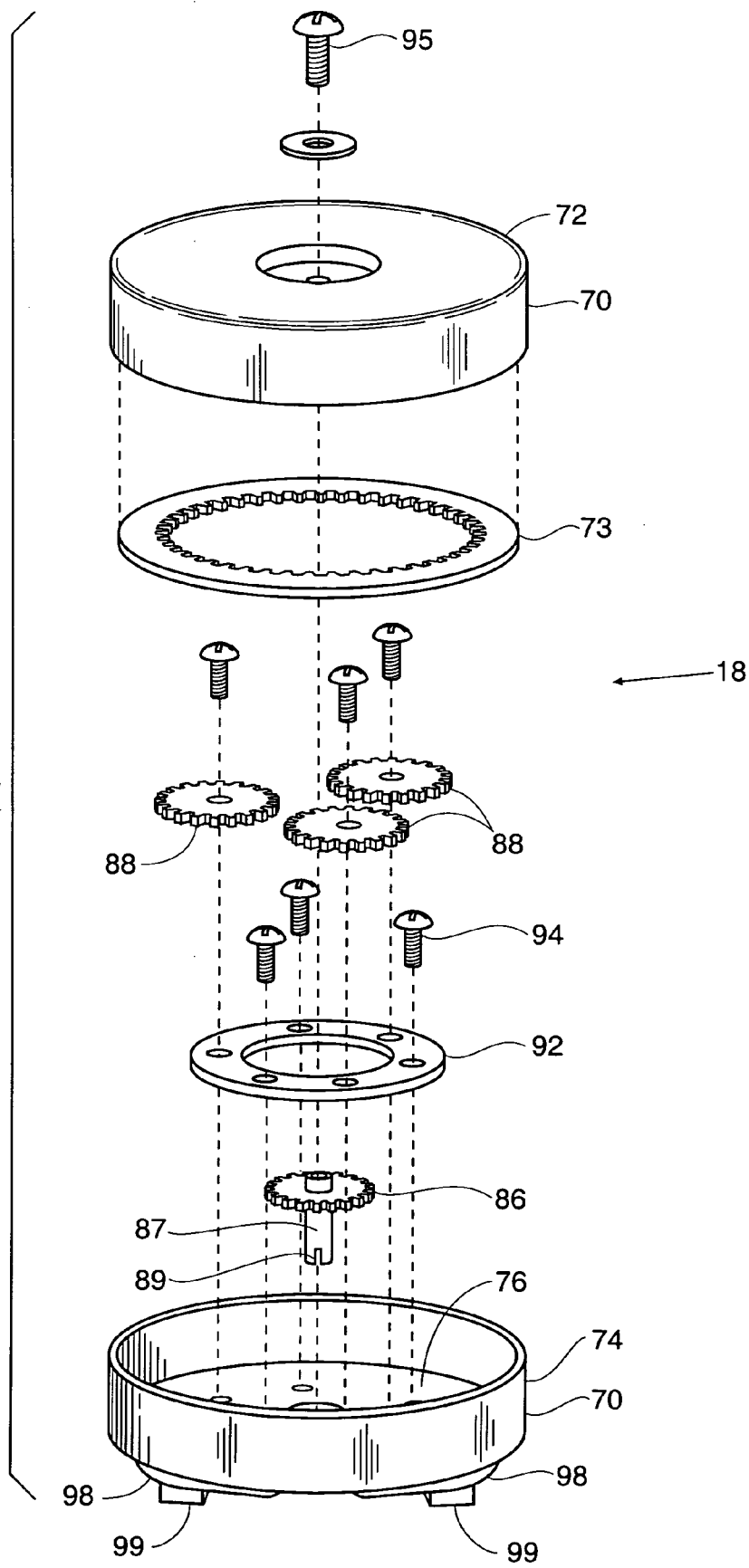
FIG. 6A is an exploded, perspective view of the actuator shown in FIG. 4.
Figure 6B:
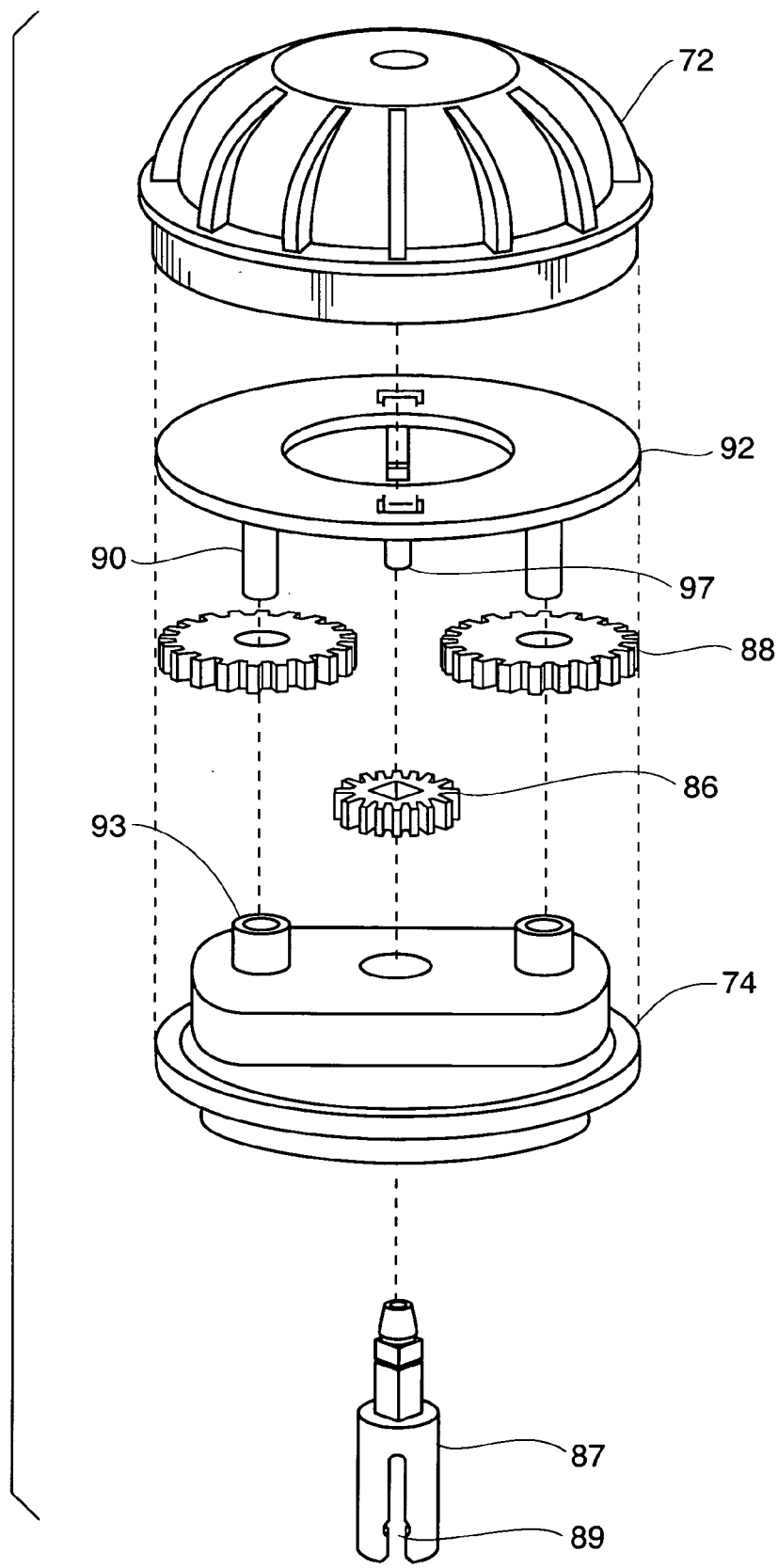
FIG. 6B is an exploded, perspective view of an alternate embodiment of an actuator.

Both the upper half 72 and the lower half 74 of the actuator 18 have an interior side 76 and an exterior side 78. As shown in FIG. 6A, the interior side 76 of the upper half 72 contains a ring gear 73. The interior side 76 of the lower half 74 contains a planetary gear arrangement 84 that meshes with the ring gear 73.

The planetary gear arrangement 84 includes a sun gear 86 and one or more planet gears 88. The sun gear 86 is fixed axially to the lower half 74 of the actuator 18 by means of a screw 95. The planet gears 88 are fixed to a retainer ring 92 by screws 94. In one alternative embodiment, the planet gears 88 would comprise two gears, each gear positioned on opposite sides of the sun gear 86.

The teeth of the planet gears 88 mesh with the teeth of the ring gear 73. The teeth of the planet gears 88 also mesh with the sun gear 86. Rotation of the upper half 72 of the actuator 18 relative to the lower half 74 of the actuator 18 rotates the ring gear 73. This, in turn, imparts rotation to the planet gears 88 within the stationary lower half 74 of the actuator 18. Rotation of the planet gears 88, in turn, rotates the sun gear 86 within the lower half 74 of the actuator 18. In the embodiment where there are three planet gears 88, a single rotation of the ring gear 73 (i.e., the upper half 72 of the actuator 18) equals approximately four rotations of the sun gear 86 within the lower half 74 of the actuator 18. In the embodiment where there are two planet gears 88, a single rotation of the ring gear 73 equals approximately three rotations of the sun gear 86.

Figure 5A:
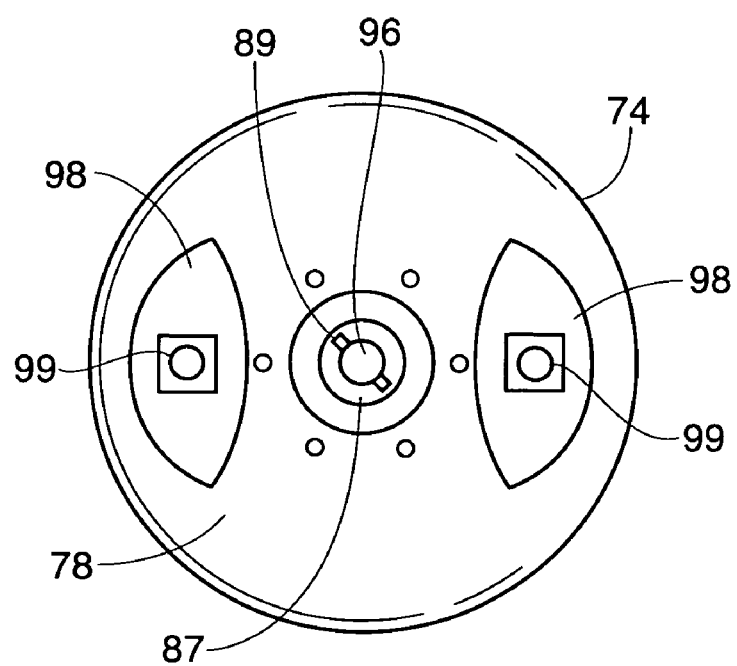
FIG. 5A is a bottom view of the actuator shown in FIG. 4.
Figure 4A:
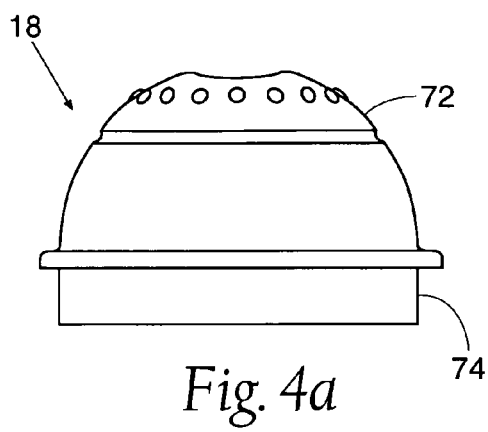
FIGS. 4A-4F are perspective side views of alternate embodiments of actuator handle designs.
Figure 4B:
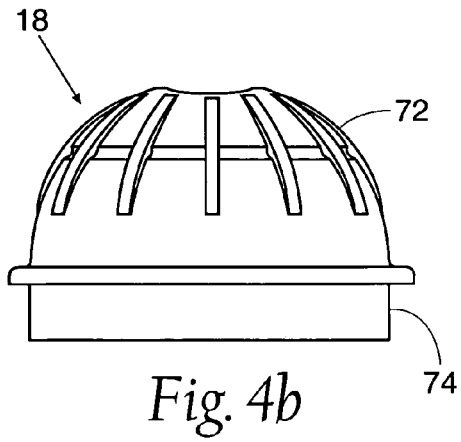
Figure 4C:
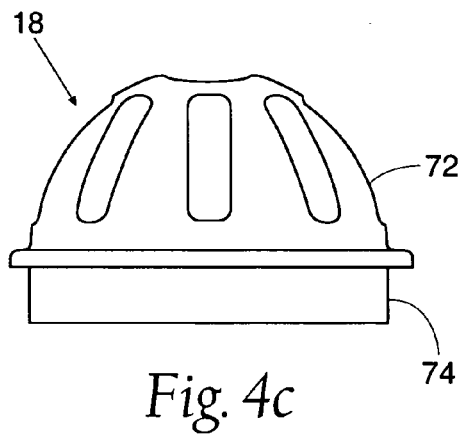
Figure 4D:
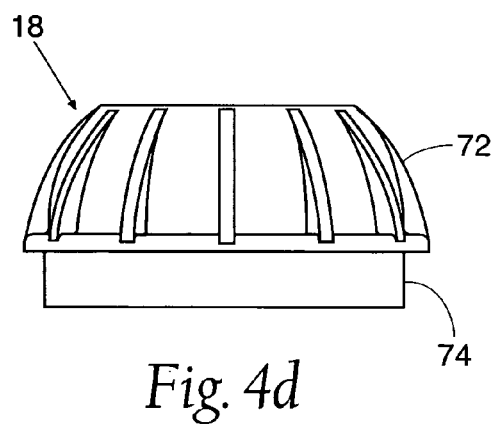
Figure 4E:
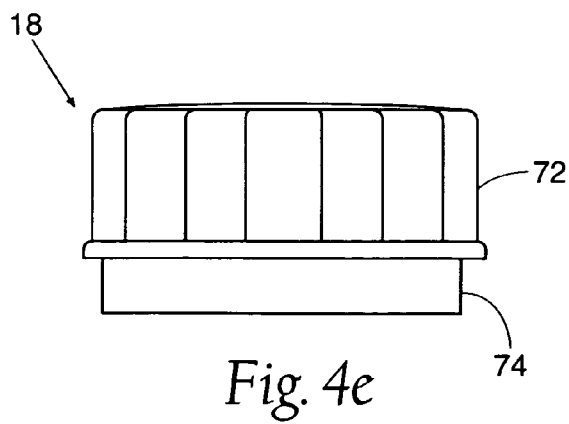
Figure 4F:
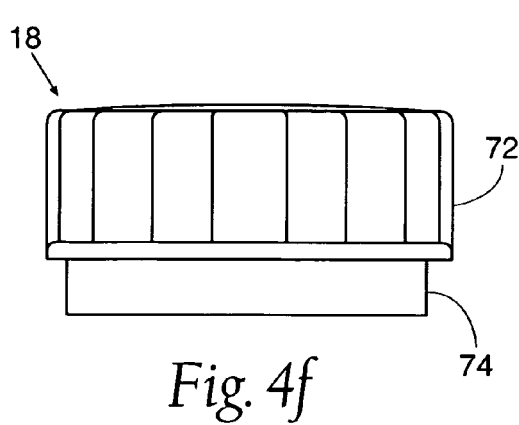

As shown in FIG. 5A, the exterior side 78 of the lower half 74 of the actuator 18 has a central slot 96 which receives the cylindrical tip 58 of the mixing element 16. An axle 87 projecting from the sun gear 86 (see FIG. 6A) extends into the slot 96. The crosspiece 60 on the tip 58 fits into a keyway 89 on the axle 87 (see FIG. 5A), which couples the mixing element 16 to the sun gear 86. Thus, rotation of the sun gear 86 imparts rotation to the mixing element 16.

Additionally, the exterior side 78 of the lower half 74 has stabilizing structure 98 (see FIG. 5A). The structure 98 abuts against and/or grips the tabs 36 of the receptacle 12 to prevent the receptacle 12 from rotating while rotation is imparted by the sun gear 86 to the mixing element 16. The stabilizing structure 98 is secured to the lower half 74 of the exterior side 78 by fasteners 99. If desired, the actuator 18 may incorporate an attachment for a standard operating room suite vacuum hose (not shown), to evacuate fumes within the receptacle 12.

Figure 18:
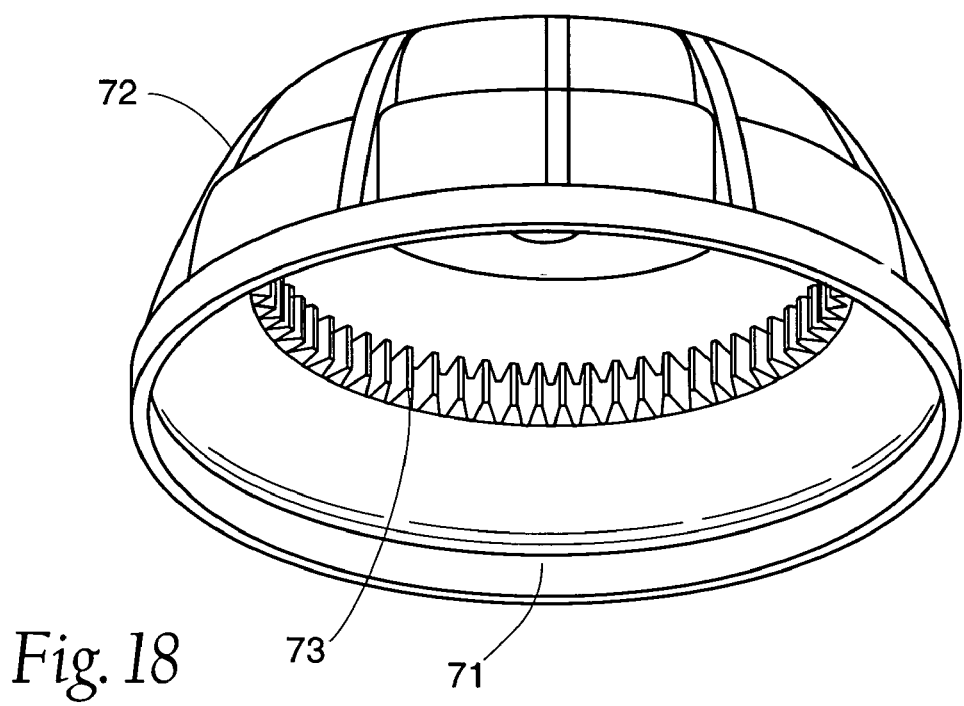
FIG. 18 is a bottom view of the upper half of the actuator that forms part of the system shown in FIG. 1B.

In an alternate embodiment (see FIG. 6B), the upper half 72 of the actuator 18 has an integral ring gear 73 adapted into the interior surface 71 (see FIG. 18) of the actuator 18. The lower half 74 of the actuator 18 has a planetary gear arrangement 84 that meshes with the ring gear 73. The planetary gear arrangement 84 includes a sun gear 86 and a plurality of planet gears 88. Desirably, the planetary gear arrangement 88 comprises two planet gears 88. The sun gear 86 is fixed axially to the lower half 74 of the actuator 18 by means of an axle 87. The axle 87 is adapted at the top to snap-fit with the upper half 72 and is adapted at the bottom to receive the tip 58 of the mixing element 16. The middle section of the axle 87 is squared off to hold the sun gear 86 in place and to receive rotational forces imparted by the sun gear 86.

The planet gears 88 are fixed to the lower half 74 of the actuator 18 by hollow gear posts 93. The retainer ring 92 has retention tabs 90 which fit through the central bore of the planet gears 88 and extend into the hollow gear posts 93 (see FIG. 6B). The retention tabs 90 have small tangs extending downward through the hollow gear posts 93 to securely engage the retainer ring 92 to the lower half 74 of the actuator 18. The retainer ring 92 also desirably has stabilizer feet 97 extending downward to provide strength and stabilization to the planetary gear arrangement 84.

Figure 5B:
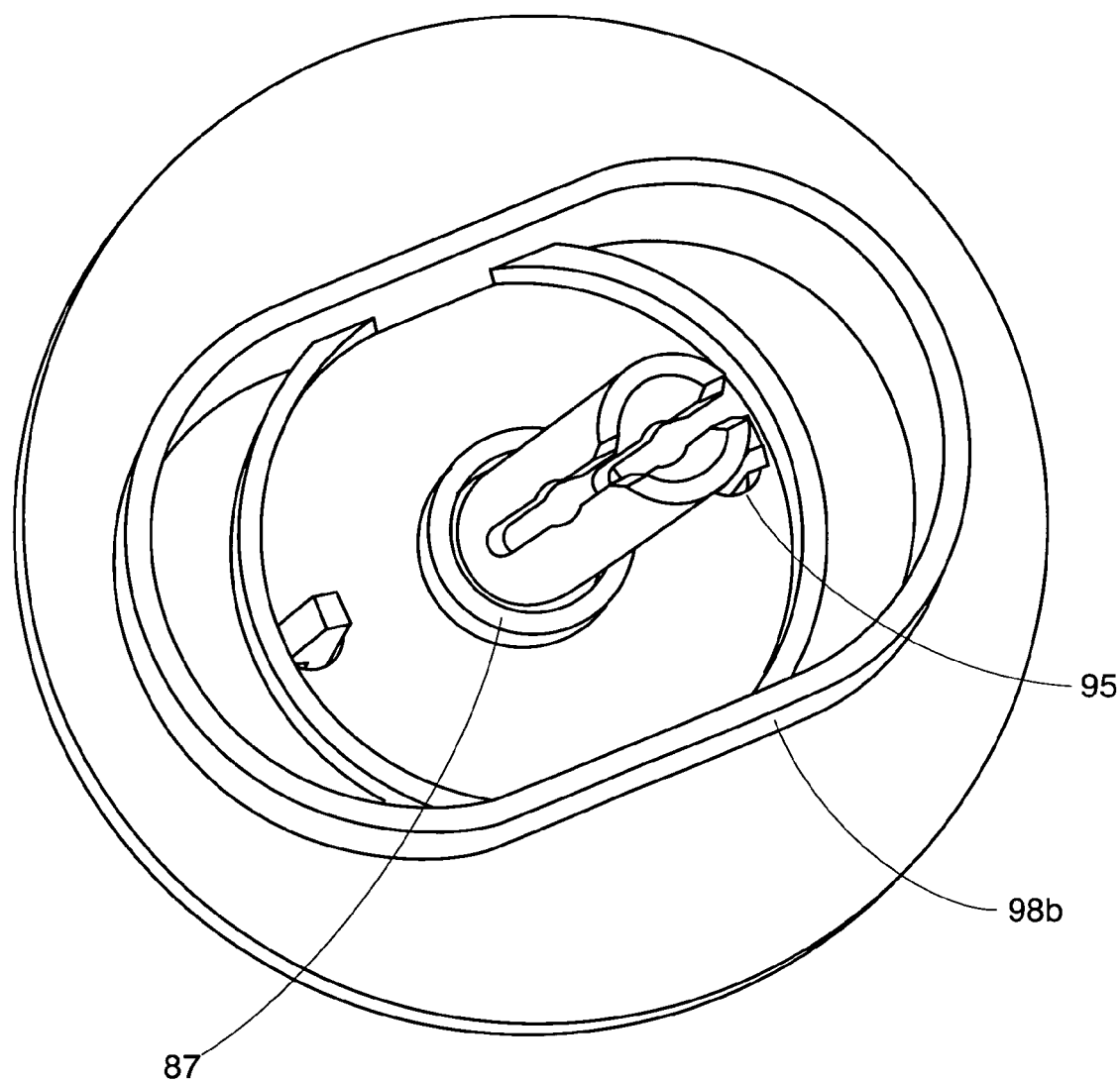
FIG. 5B is a bottom view of an alternate embodiment of an actuator.

As shown in FIG. 5B, the exterior side 78 of the lower half 74 of the actuator 18 has a stabilizing structure 98B which is generally oblong to accommodate insertion of the receptacle 12. The oblong shape of the stabilizing structure 98B prevents the receptacle 12 from rotating while rotation is imparted by the sun gear 86 to the axle 87 which couples to the mixing element 16.

E. The Plunger

Figure 14:
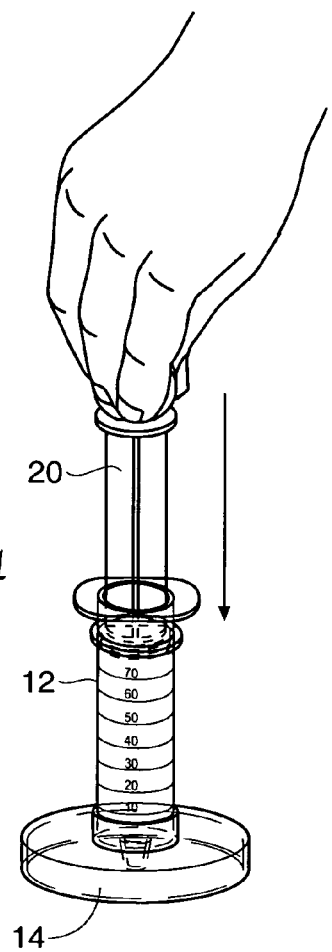
FIG. 14 is a perspective view showing the plunger being inserted into the receptacle after the materials have been mixed in the receptacle.
Figure 16:
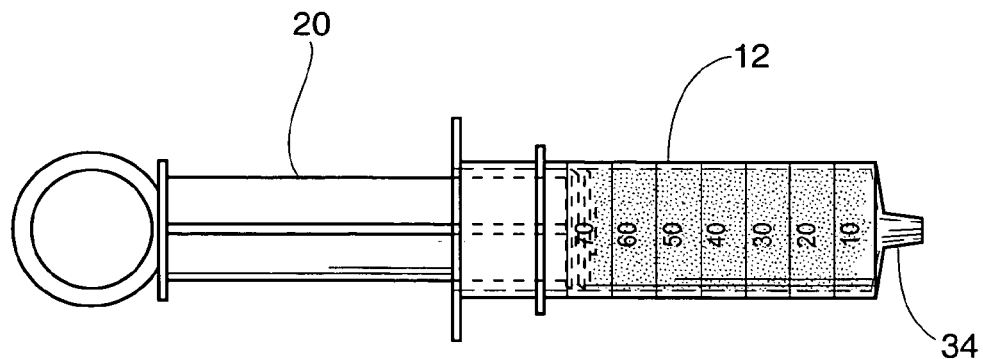
FIG. 16 is a perspective view of the plunger inserted into the receptacle containing the material, which is now ready to be dispensed.

The plunger 20 (see FIGS. 14 and 16) fits into the bore 37 of the receptacle 12. Advancement of the plunger 20 within the receptacle 12 desirably expels air from the receptacle 12, as well as dispenses material from the receptacle 12.

Figure 19:
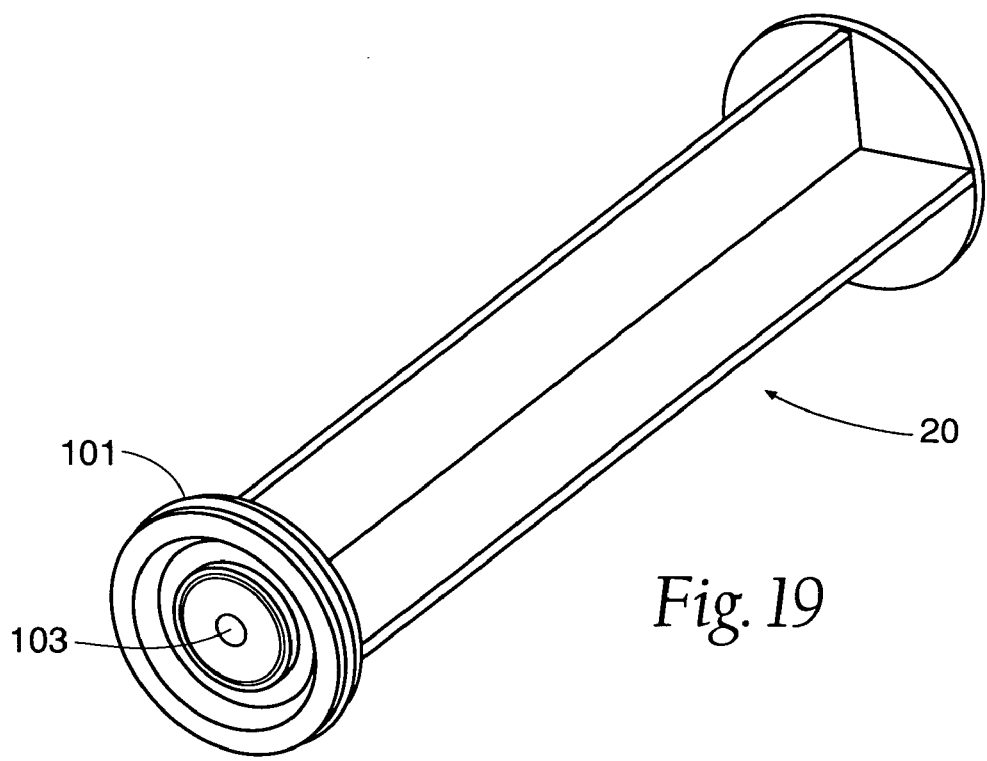
FIG. 19 is a perspective view of the plunger assembly showing an opening for an air purge valve.

As shown in FIG. 19 the plunger 20 may also desirably contain one or more openings 103 for a valve that automatically purges the air in the receptacle 12 between the plunger 20 and mixed bone filling material. The plunger 20 can contain a seal 101 made from various materials including, but not limited to, a non-rigid material that is unaffected by contact with the mixed bone filling material. In one embodiment, the plunger 20 can contain a valve with a small ball bearing (not shown) which allows air to escape as the plunger 20 is advanced through the receptacle 12. The ball bearing (not shown) may be made from a plastic material that is less dense than the bone filling material. As the plunger 20 contacts the viscous bone filling material, the ball bearing is forced up into a closed position. Purging the air allows for direct contact between the plunger 20 and material, which provides for improved dispensing control of the material.

F. The Dispensing Element

Figure 17:
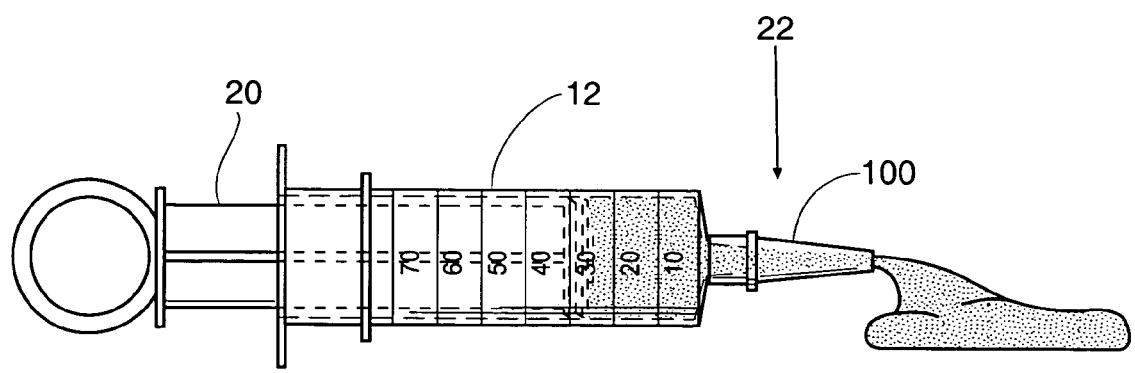
FIG. 17 is a perspective view of the material mixed within the receptacle being dispensed from the receptacle.

In the system shown in FIG. 1A, the dispensing element 22 comprises a nozzle 100 that is adapted to fit on the distal tip 34 of the receptacle 12 (see FIG. 17). In another embodiment, a LUER® fitting (not shown) is incorporated into the distal tip 34 of the receptacle 12. In another embodiment, a fitting (not shown) is incorporated into the distal tip 34 of the receptacle 12, the fitting being adapted to mate with the body of a 5 cc or 10 cc syringe. In another embodiment, tubing (not shown) is incorporated into the distal tip 34 of the receptacle 12, the tubing being adapted to fit within a 5 cc or 10 cc syringe body.

Figure 20:
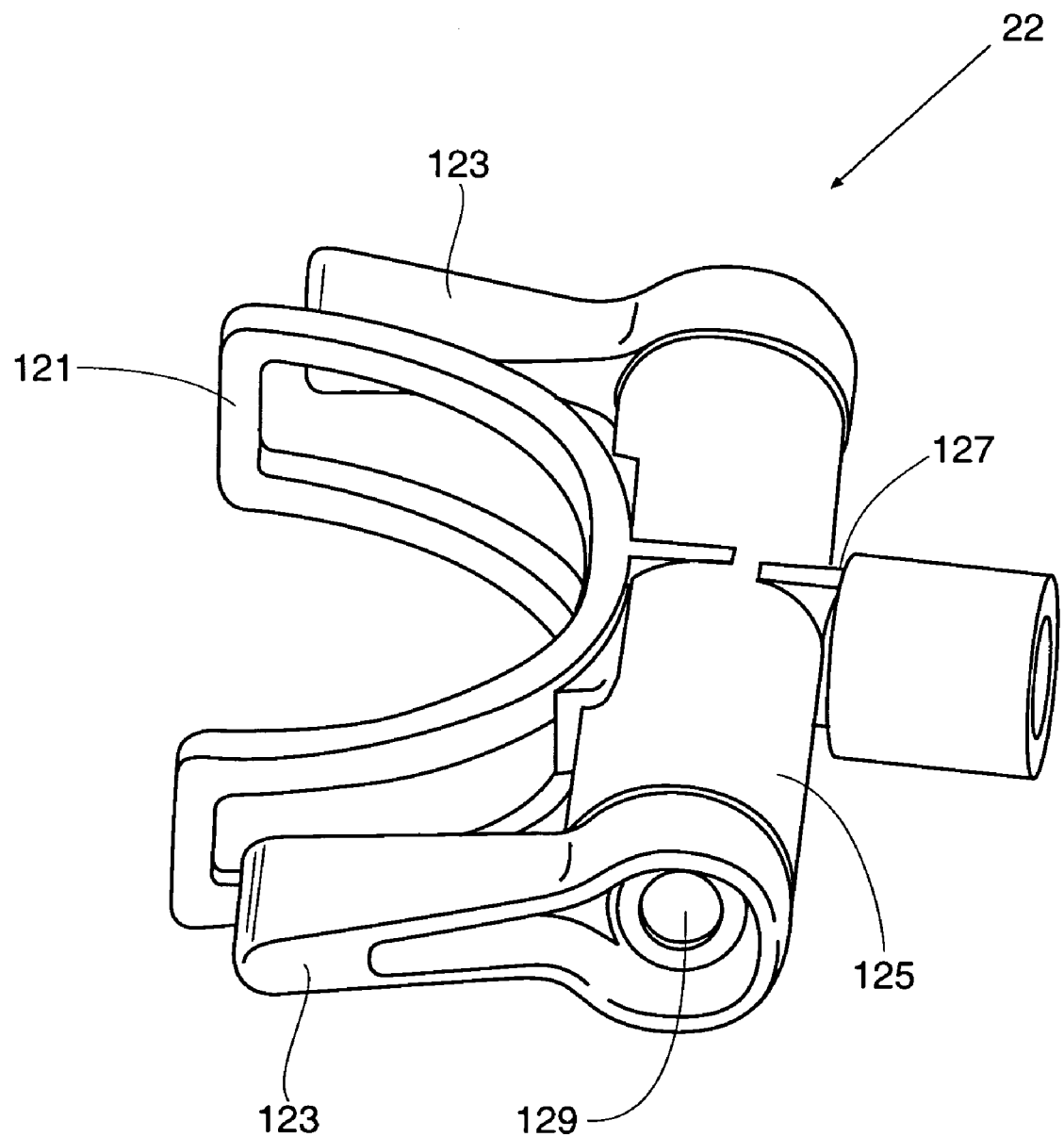
FIG. 20 is a perspective view of one embodiment of a dispenser valve with an assembly for securing to the receptacle of FIG. 2B.
Figure 21:
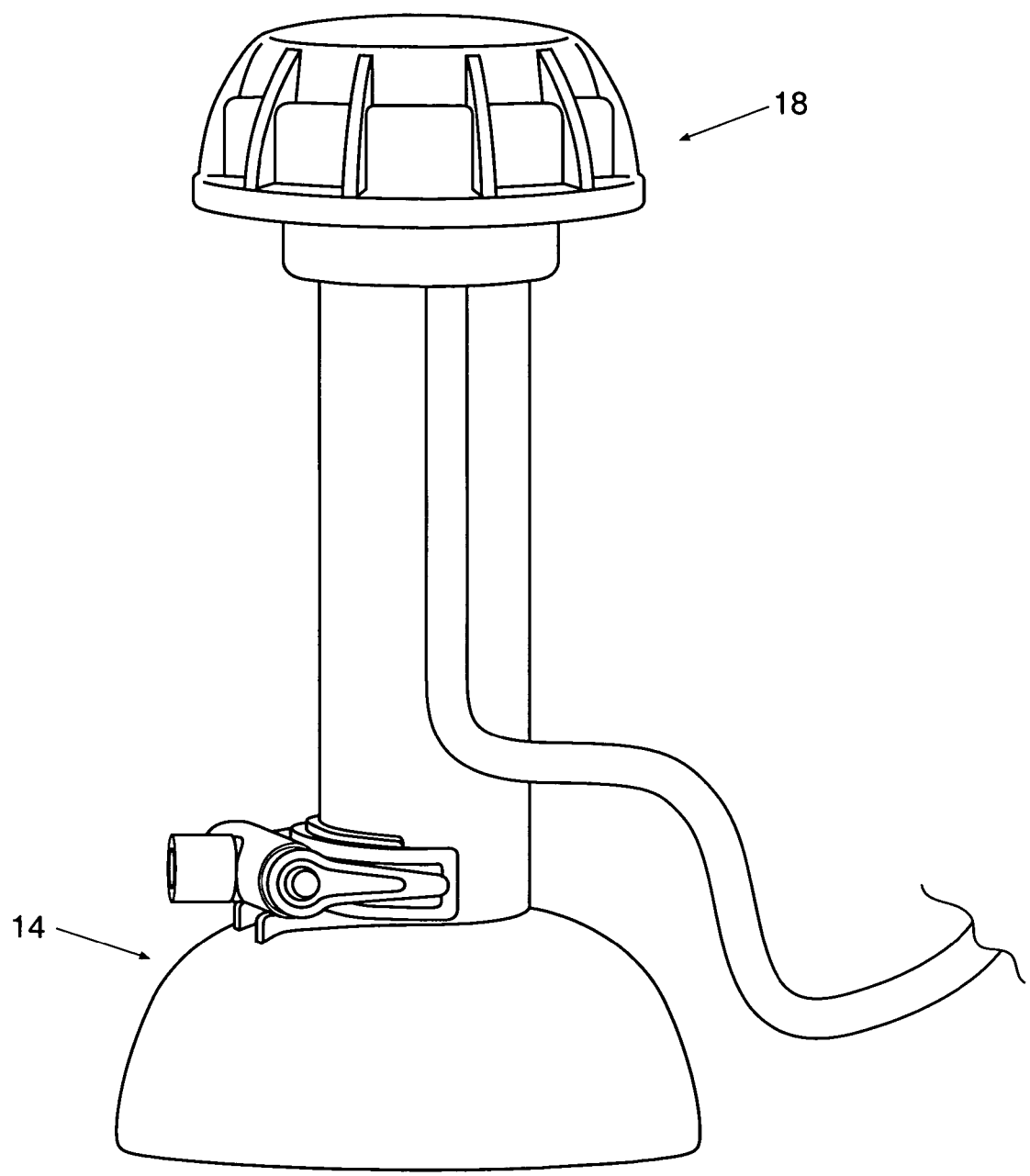
FIG. 21 is a perspective view of the receptacle of FIG. 2B with an optional attached vacuum line.

In the system shown in FIG. 1B, the dispensing element 22 desirably snap fits onto the distal end 32 of the receptacle 12 by means of clips 121 (see FIG. 20). The dispensing element 22 may also be attached to the receptacle 12 by other means, such as with adhesive, welding or by other means known in the art. The dispensing element 22 desirably mates with the outlet 34B of the receptacle 12 (see FIG. 2B). A stopcock valve (not shown), or other type of suitably valve, can be located inside the valve body 125 and have a outlet 127 for the mixed material. The dispensing element 22 can have one or more dispensing handles 123 located at the end(s) of the valve body 125. Two dispensing handles 123, as shown in FIG. 20, can allow for either right- or left-handed operation of the dispensing element 22. A LUER® fitting 129 is desirably incorporated onto the valve body 125, to facilitate attachment of a syringe or threaded bone filling device. Of course, any number of other types of fittings or tubings could be incorporated onto the valve body 125, depending upon the type of instrument receiving the transferred mixed material.

G. The Measuring Device

The measuring device 24 (see FIG. 1A) is used to measure components before placing the components into the receptacle for mixing. The measuring device 24 may be of a fixed size, such as a 10 cc measuring cup, may be graduated, and/or may include a sieve for sifting particles before mixing.

H. The Funnel

The funnel 10 is used to facilitate placing or pouring of the components to be mixed into the receptacle 12 (see FIG. 1B).

II. Illustrative Use of the System

Figure 10:
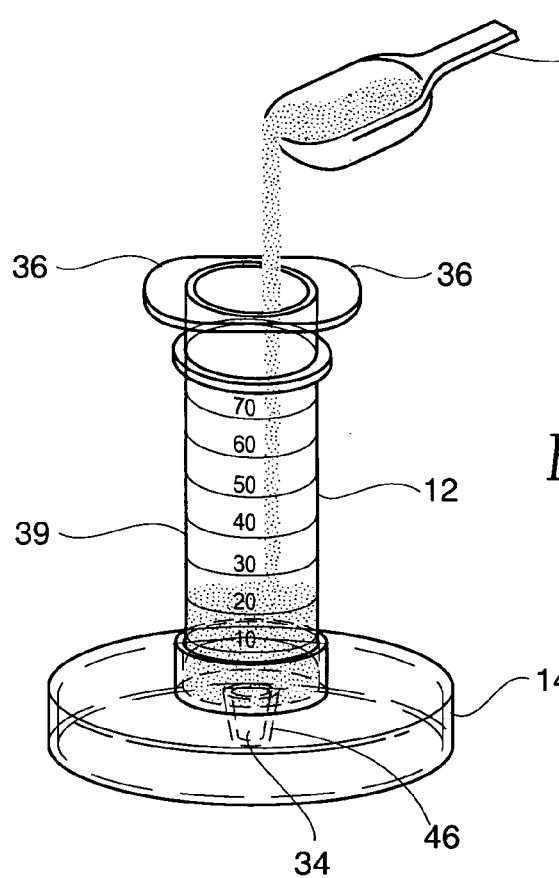
FIG. 10 is a perspective view of the receptacle shown in FIG. 2 inserted into the stand shown in FIG. 3, and also showing a component being added to the receptacle.

In the embodiment shown in FIG. 1A, the receptacle 12, stand 14, mixing element 16, actuator 18, plunger 20, dispenser 22 and the measuring device 24, as well as the components to be mixed, are gathered together for use, or are withdrawn as needed from the kit 200. The physician or an assistant inserts the distal end 32 of the receptacle 12 into the neck 44 of the upper side 40 of the stand 14 (see FIG. 10). Desirably, the distal tip 34 of the receptacle 12 is held within the small chamber 46 located on the upper side 40 of the stand 14, desirably sealing the distal tip 34 closed.

As FIG. 20 shows, the physician may use the measuring device 24 to measure a component to be mixed, such as a powdered component for poly(methyl methacrylate) bone cement. The powdered component is poured into the receptacle 12. If the receptacle 12 bears a graduated scale 39 on its outer surface 33, the component can be added to the receptacle 12 until the desired level is reached. After the powdered component is added to the receptacle 12, another component, such as a liquid monomer for bone cement, is added.

Figure 11:
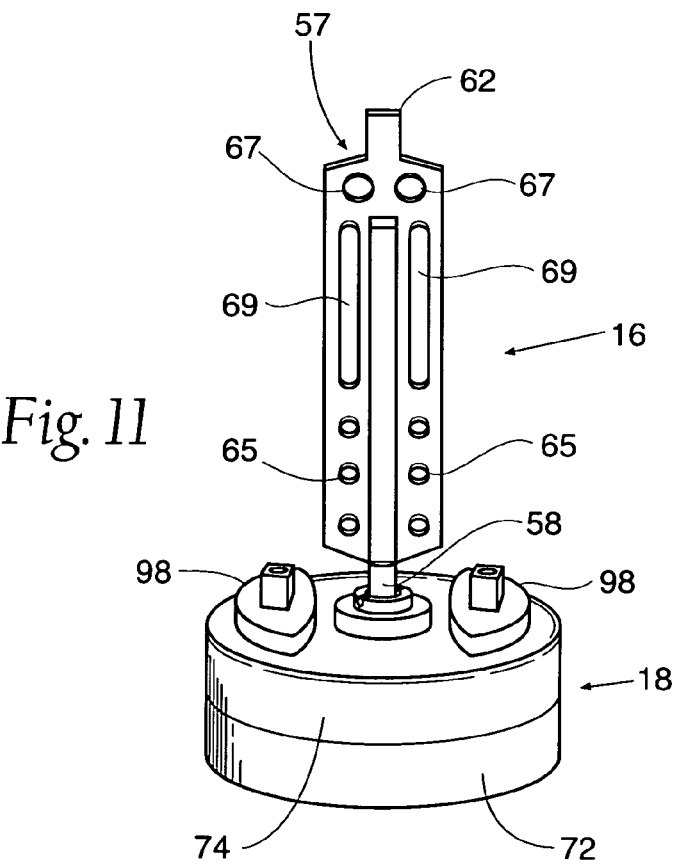
FIG. 11 is a perspective view of the proximal end of the mixing element shown in FIG. 8 inserted into the exterior side of the lower half of the actuator shown in FIG. 4.
Figure 12:
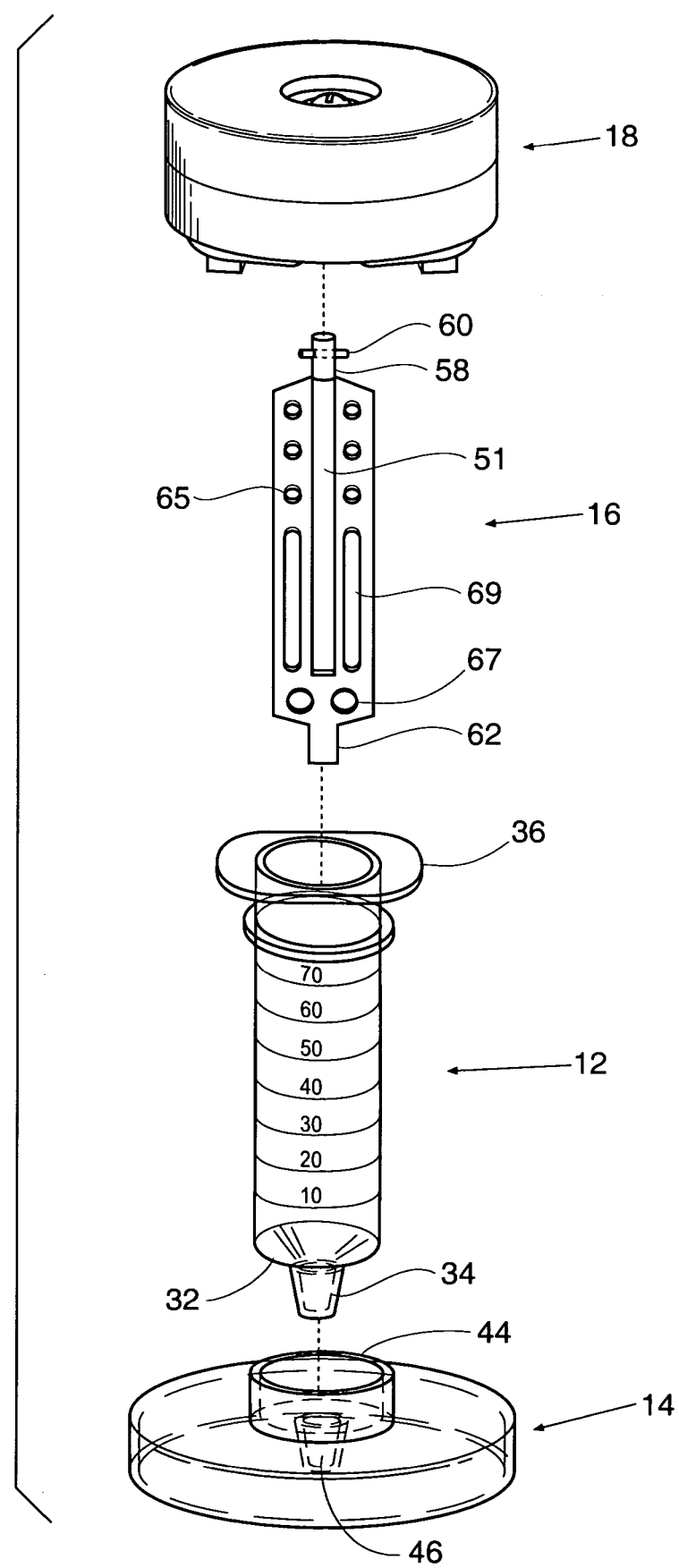
FIG. 12 is an exploded view of the actuator, mixing element, receptacle, and stand assembly, as also shown in assembled view in FIG. 13.

The mixing element 16 and actuator 18 are then obtained. Desirably, the proximal end 56 of the mixing element 16 has been inserted into the slot 96 located on the exterior side 78 of the lower half 74 of the actuator 18 (as FIG. 11 shows). The assembly is now inverted and the distal end 57 of the mixing element 16 inserted into the proximal end 30 of the receptacle 12 (shown in exploded view in FIG. 12). Desirably, the mixing element 16 is inserted such that the distal tip 62 of the mixing element 16 extends into the distal tip 34 of the receptacle 12. The actuator 18 desirably engages with the tabs 36 located on the proximal end 30 of the receptacle 12, so that the lower half 74 of the actuator 18 remains stationary relative to the receptacle 12.

Figure 13:
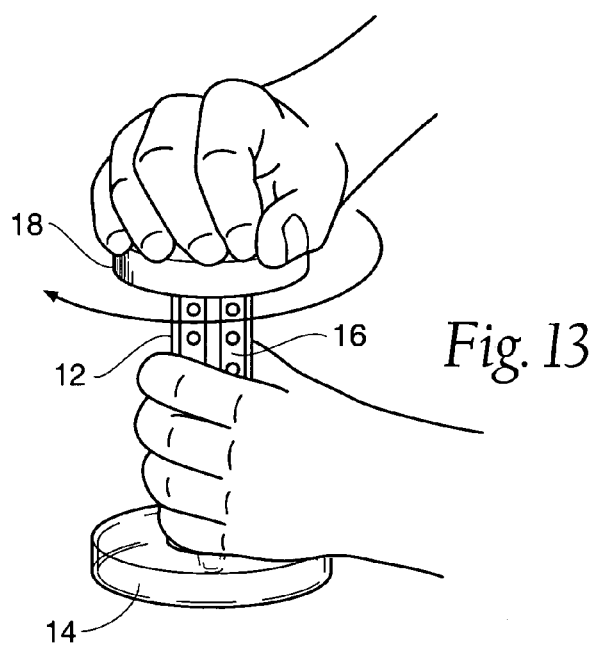
FIG. 13 is a perspective view of the assembly shown in FIG. 12, showing the actuator grasped by one hand and being manually rotated, and showing the receptacle being grasped by the other hand of the operator, the rotation of the actuator serving to mix materials in the receptacle.

The physician now grasps the upper half 72 of the actuator 18 with one hand, while holding the stand 14, the receptacle 12 or the stand 14 and receptacle 12, with the other hand (see FIG. 13). The upper half 72 of the actuator 18 is then rotated back and forth, first clockwise and then counterclockwise, e.g. (or vice versa), by half-turns, relative to the receptacle 12. Alternatively, or in conjunction with this back and forth motion, the actuator 18 may be rotated in a single direction. Desirably, the actuator 18 is rotated enough times to adequately mix the mixture.

Figure 15:
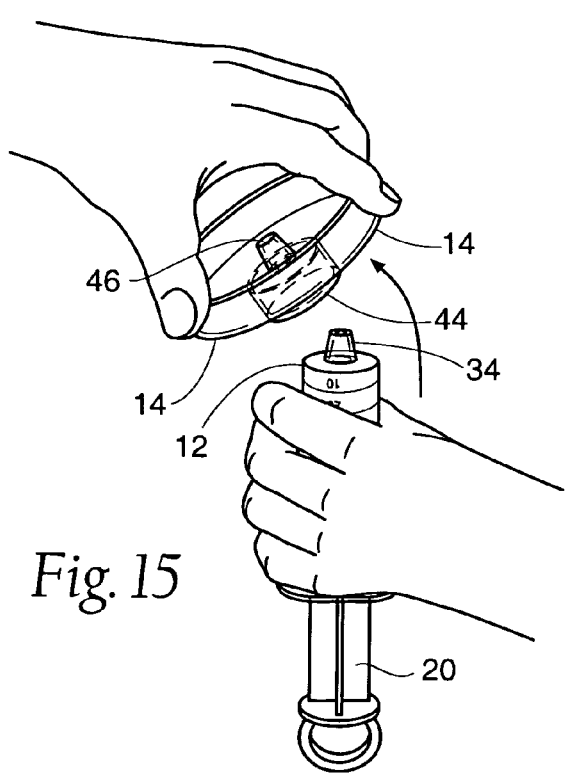
FIG. 15 is a perspective view showing the stand being removed from the receptacle prior to dispensing material from the receptacle.

After the mixture is adequately mixed, the actuator 18 and mixing element 16 are removed from the receptacle 12 and set aside. If desired, the mixing element 16 may be scraped against the top of the receptacle 12 to remove mixture clinging to the element 16, desirably returning such mixture to the receptacle 12. Next, the plunger 20 is inserted into the proximal end 30 of the receptacle 12 (see FIG. 14). The assembly can now be safely inverted and the stand 14 removed from receptacle 12 (see FIG. 15). Desirably, the stand 14 will not be removed from the receptacle 12 before the step of inserting the plunger 20 and inverting the assembly. In such a case, the mixture, as in the case of a bone filling mixture, could easily flow out of the opening in the distal tip 34 of the receptacle 12.

After the stand 14 is removed from the receptacle 12, air can be expelled from the distal tip 34 of the receptacle 12 by advancing the plunger 20 in the usual fashion of purging air from a syringe. The mixture may be dispensed directly from the receptacle 12 by advancing the plunger 20. If desired, a dispenser 22 is fitted onto the distal tip 34 of the receptacle 12. In one embodiment, if the dispenser 22 is a nozzle 100, the mixture is dispensed through the nozzle 100. In another embodiment, if the distal tip 34 of the receptacle 12 incorporates a LUER® fitting, the LUER® fitting may mate with a bone filler device as disclosed in U.S. Pat. No. 6,241,734 (which is incorporated herein by reference). When the LUER® fitting is incorporated into the distal tip 34 of the receptacle 12, the combination allows for the direct filling of multiple bone filler devices. In another embodiment, if the distal tip 34 of the receptacle 12 incorporates a fitting that mates with a syringe body of a 5 cc or 10 cc syringe, the syringe may be filled with the mixture in the receptacle 12. In another embodiment, the distal tip 34 of the receptacle 12 may incorporate tubing which fits within a 5 cc or 10 cc syringe body, thus allowing the syringe to be back-filled from the plunger end. In such an embodiment, the tubing is inserted through the plunger opening of the syringe. The syringe is filled from its distal tip to its proximal end, the tubing being withdrawn as the syringe fills to a desired level.

The system shown in FIG. 1B contains additional features with enhanced ease of use and fewer steps. The receptacle 20 is packaged in the kit 200 with the dispensing element 22 in the closed position. After gathering the system parts (receptacle 12, mixing element 16, actuator 18, plunger 20 and funnel 10) from the sealed kit 200 as well as the material to be mixed, the physician or an assistant positions the funnel 10 within the proximal end 30 of the receptacle 12 and pours the powdered component into the receptacle 12. If desired, additional powdered materials, such as sterile barium sulfate (to make the mixture radiopaque) or antibiotics (to prevent infection) may be added to the receptacle 12 before addition of the liquid monomer. The mixing element 16 and actuator 18 are coupled together as previously described and inserted into the receptacle 12. The actuator 18 is positioned to engage with the tabs 36 on the proximal end 30 of the receptacle 12. The physician or an assistant now rotates the actuator 18 to mix the material as previously described. The monomer fumes in the receptacle 12 may be desirably evacuated from the receptacle 12 by the vacuum hose attachment 31. After the mixture is adequately mixed, the actuator 18 and mixing element 16 are removed from the receptacle 12 and set aside. Next, the plunger 20 is inserted into the proximal end 30 of the receptacle 12. Air can be automatically purged from the system through the openings 103 in the plunger 20. The residual air/monomer mixture may then be evacuated from the interior bore 37 of the receptacle 12 by the vacuum hose attachment 31, further reducing exposure of the physician or an assistant to the monomer fumes. The mixture is now ready to be transferred. Desirably, the mixed material is transferred directly to the bone filler device as disclosed in U.S. Pat. No. 6,241,734. This step eliminates the need for transferring the material to another device, such as a syringe, which would in turn be used to fill the device of U.S. Pat. No. 6,241,734. The mixture may be dispensed directly through the opened dispensing element 22 by pushing down on the plunger 20. Alternatively, the flow of the mixture may be controlled by rotating the dispensing handles 123 to open and close the stopcock valve (not shown).

If a mixture of additional bone filler material is desired, or additional bone filler material is required after the initial mixture has hardened and/or become unusable, the used mixing element 16 (having bone filler material thereon) may be removed from the actuator 18 and replaced with a new mixing element 16, allowing the actuator 18 to be used to mix an additional batch of bone filler material. In such a case, the kit 200 could contain a single actuator 18 and measuring device 24, with multiple receptacles 12, stands 14, mixing elements 16, plungers 20 and dispensing elements 22 to allow mixing of multiple batches of bone filler material.

III. Closed Cement Mixing and Transfer System

Where the release of fumes and/or vapors from a surgical material is undesirable for some reason, it may be advantageous to use a closed mixing and transfer system for the preparation and/or delivery of medical materials such as bone cement. For example, the fumes and/or vapors from the liquid monomer component of PMMA bone cements can have a very unpleasant smells and inhalation of these fumes may pose a significant health risk to various operating room personnel as well as the patient.

In the case of bone cement comprising PMMA powder and liquid monomer components, the liquid monomer is typically sealed within a glass jar or ampoule prior to use while the powder is contained in a plastic bag. One example of such packaging is found with SimplexP® PMMA bone cement, commercially available from Howmedica Corporation. While the powdered component of such bone cement is generally inert and not prone to becoming airborne (unless sufficiently disturbed), the liquid monomer component has a very low vapor pressure and vaporizes readily in contact with air.

Once a glass ampoule containing liquid monomer is opened (typically by breaking the frangible cap on the glass ampoule) the liquid monomer is exposed to the atmosphere and begins to vaporize immediately. Moreover, during the mixing process, the liquid monomer continues to vaporize and also outgasses from the liquid/powder mixture. Once mixing is completed, the monomer continues to outgas from the liquid/powdered mixture, until such time as the mixture is contained within an enclosed environment (such as a syringe or other closed dispensing device or when the mixture is placed within the patient's body). Unless the mixture is contained within an enclosed environment during substantially all of the steps of the mixing and delivery operation, therefore, a significant amount of vaporized monomer may be released to the operating room during mixing and dispensing of bone cement.

Figure 22:
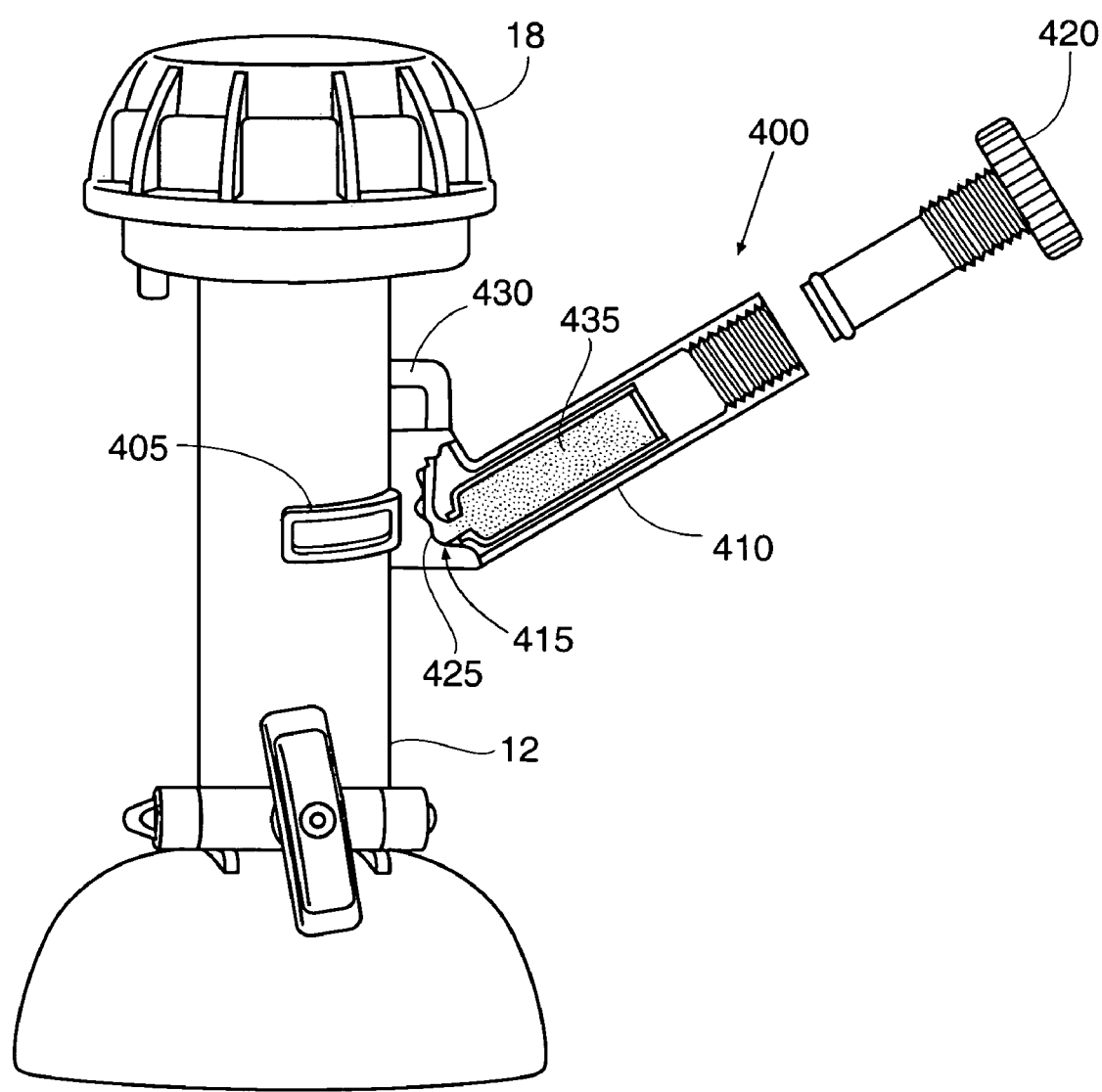
FIG. 22 is a partially cut-away view of the receptacle of FIG. 21.
Figure 23:
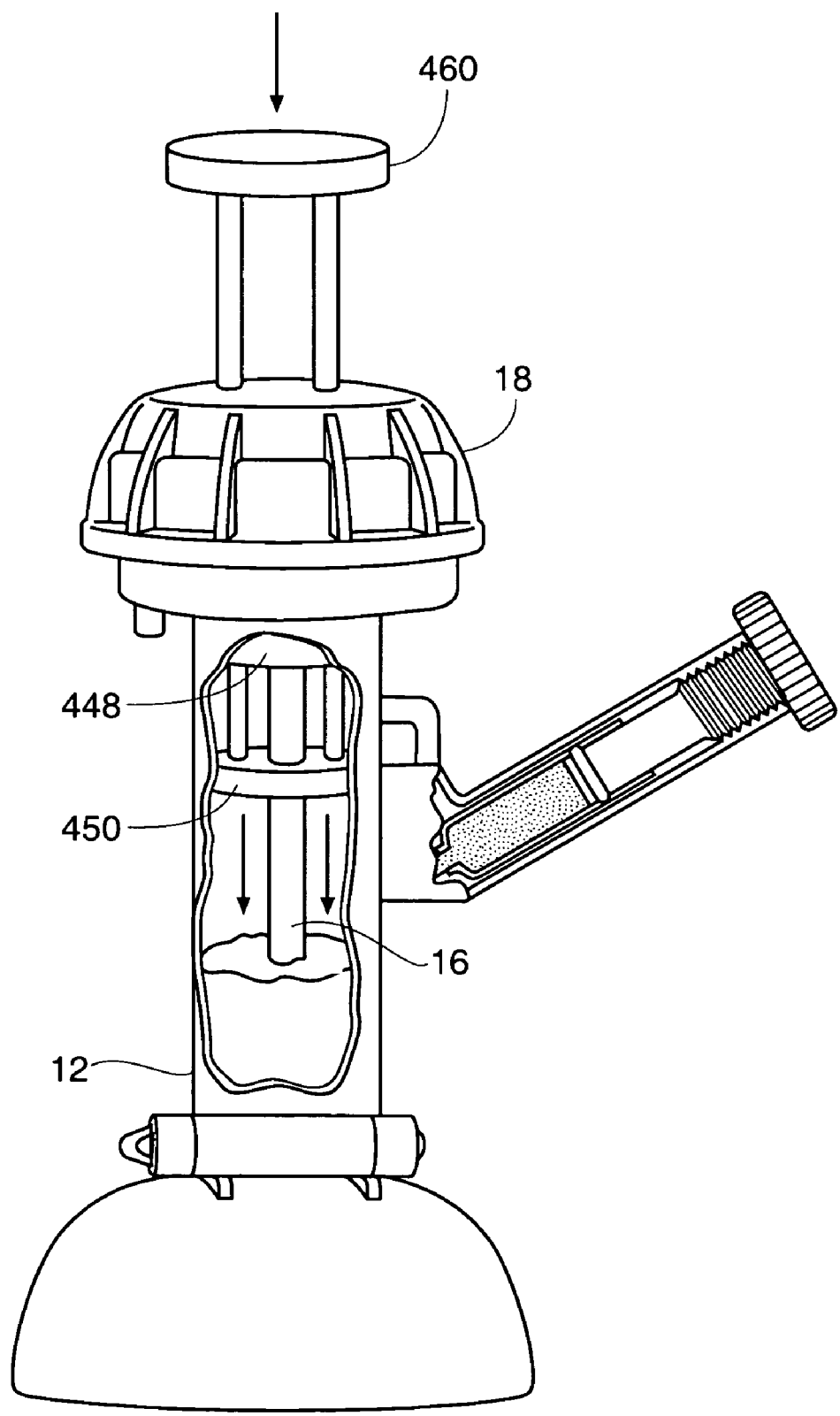
FIG. 23 is another partially cut-away view of the receptacle of FIG. 21.

FIGS. 22 and 23 depict an alternate embodiment of a cement mixing and transfer system which desirably minimizes the release of vaporized monomer to the operating room environment. In this embodiment, the receptacle 12 incorporates a monomer dispensing body 400. The monomer dispensing body 400 comprises a retaining clip 405, a containment tube 410, a breaking element 415, a cap 420, a supply lumen 425 and a vent lumen 430. Desirably, the dispensing body is secured to the receptacle 12, with the supply lumen 425 and vent lumen 430 communicating with the interior of the receptacle 12 through one or more openings (not shown) in the receptacle wall. The dispensing body 400 may be secured to the receptacle in various ways, including clips, adhesive, welding or by other methods known in the art.

As shown in FIG. 23, a stationary seal 448 desirably engages the upper opening of the receptacle 12 in an air-tight fashion, desirably sealing the receptacle 12 from the operating room environment. A sliding seal 450 is desirably positioned below the stationary seal 448 and within the receptacle 12. These seals 448 and 450 can comprise various known sealing materials, including latex rubber. Desirably, the seals 448 will permit rotation of the mixing element 16 and axle 87 while maintaining a substantially air-tight seal between the receptacle contents and the atmosphere. In addition, the sliding seal 450 can desirably be moved longitudinally within the receptacle 12. If desired, the sliding seal can incorporate an internal slot or opening (not shown), which permits the sliding seal 450 to slide along the central axis of the mixing element 16 while maintaining a substantially air-tight seal with the mixing element 16.

To prepare the bone cement mixture, a measured amount of powdered PMMA component is introduced into the receptacle 12. The mixing element and actuator are then attached to the receptacle, with the seals 448 and 450 sealingly engaging the receptacle 12. A sealed glass ampoule 435 containing liquid monomer is inserted into the containment tube 410. The cap 420 is placed on the tube 410, sealing the containment tube closed.

The cap 420 is then tightened onto the ampoule 435, desirably forcing the ampoule 435 against the breaking element 415 and fracturing the ampoule 435. Liquid monomer will desirably flow into the containment tube, through the supply lumen 425 and into contact with the powdered component within the receptacle 12. The vent lumen 425 will desirably relieve any vacuum which could be formed in the containment tube.

The liquid and powdered components are now mixed in the manner previously described. Once mixing is completed, a plunger 460 can be inserted through openings (not shown) in the actuator 18 and stationary seal 448 whereby the sliding seal 450 can be advanced towards the mixture within the receptacle 12. If desired, the sliding seal 450 can incorporate a labyrinth seal or other arrangement which permits air to flow past the sliding seal. Desirably, any air and/or vaporized monomer which flows past the sliding seal 450 will be contained by the stationary seal 448. Once in contact with the PMMA mixture, the sliding seal 450 will desirably pressurize the mixture, which can then be dispenses in the previously described manner.

With this embodiment, the PMMA mixture can be dispensed from the mixing and dispensing system without significant release of monomer fumes. Once dispensing is complete, the entire closed system may be disposed of safely.

Figure 25:
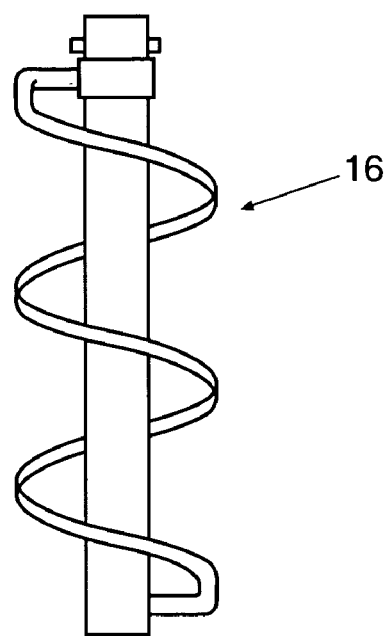
FIG. 25 is a perspective view of another embodiment of a collapsible mixing element suited for use in the receptacle of FIG. 21.
Figure 24A:
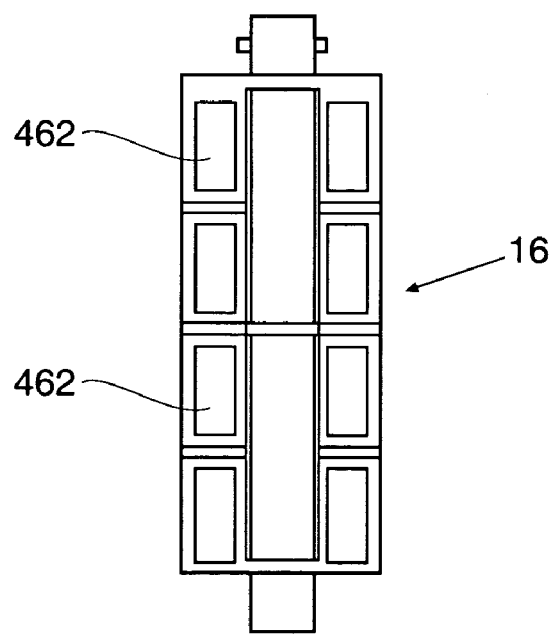
FIG. 24A is a perspective view of an embodiment of a collapsible mixing element suited for use in the receptacle of FIG. 21.
Figure 24B:
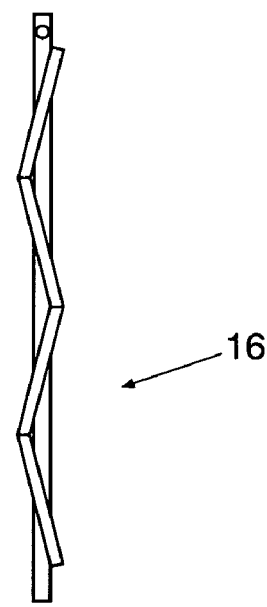
FIG. 24B is a side view of the collapsible mixing element of FIG. 24A.
Figure 26:
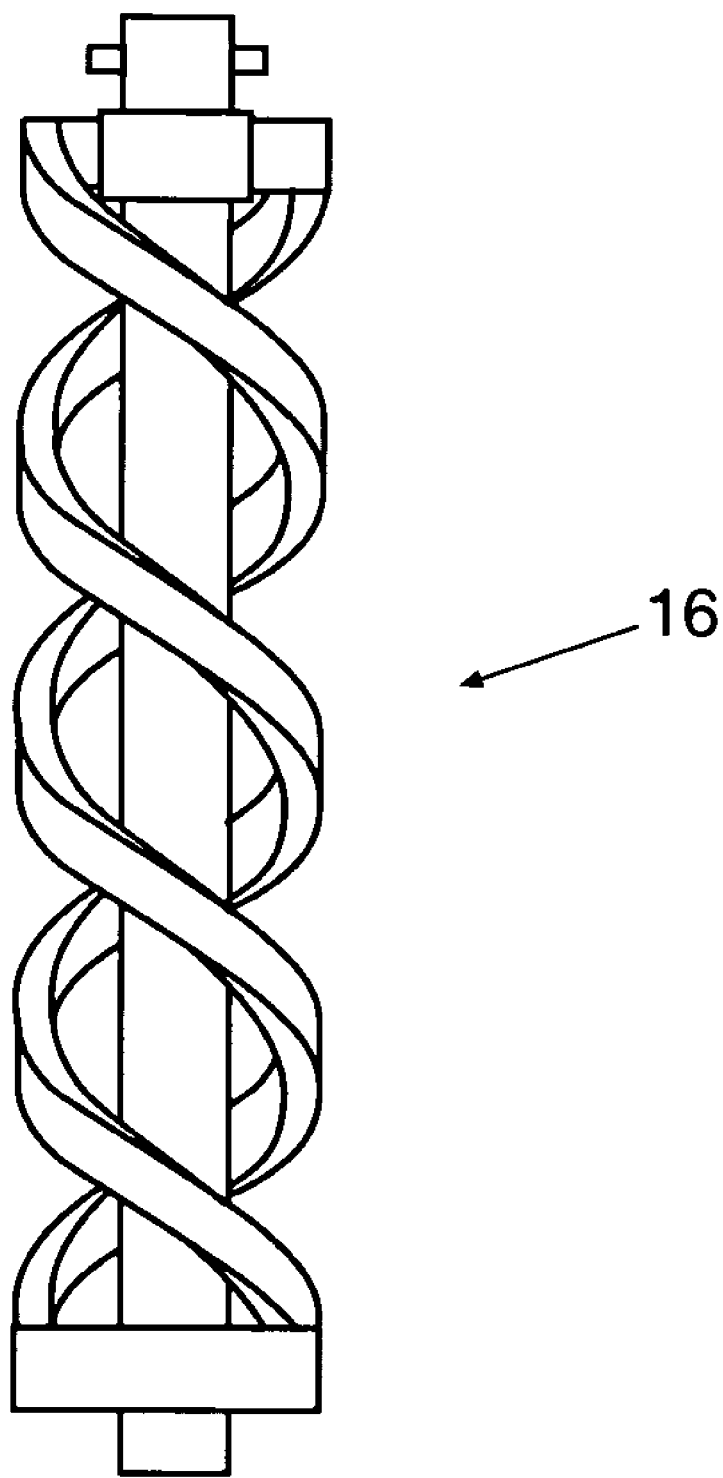
FIG. 26 is a perspective view of another embodiment of a collapsible mixing element suited for use in the receptacle of FIG. 21.

FIGS. 24A, 24B, 25 and 26 depict various embodiments of mixing elements useful in conjunction with the previously-described closed mixing and transfer system. These mixing elements are particularly well suited to collapse and/or folding after mixing has been completed to facilitate advancement of the sliding seal 450 and dispensing of the PMMA mixture. More specifically, FIGS. 24A and 24B depict views of a mixing element 16 comprising a series of sections 460 which mix the PMMA components in response to rotation of the mixing element but, when compressed, desirably fold in an accordion-like fashion to allow advancement of the sliding seal 450 and dispensing of the PMMA mixture. FIG. 25 depicts a mixing element 16 comprising a helical section which mixes the PMMA components in response to rotation of the mixing element 16 but, when compressed, desirably compresses in a spring-like fashion to permit advancement of the sliding seal 450 and dispensing of the PMMA mixture. FIG. 26 depicts a mixing element 16 comprising a plurality of helical sections which operate in a similar fashion.

The features of the invention are set forth in the following claims.

I claim:

1. A system comprising:

a receptacle having a sidewall peripherally surrounding an interior for receiving components of a bone filling material in an unmixed condition, the receptacle including a first end region and a second end region oppositely spaced from the first end region;

a dispenser outlet formed on the sidewall adjacent the second end region and communicating with the interior of the receptacle;

base means on the second end region for supporting the first end region in an upright condition and being sized and configured for resisting tipping of the receptacle during use;

mixing element means sized for insertion into the interior of the receptacle through the first end region while the base means supports the first end region in the upright condition, to mix the components of the bone filling material within the interior of the receptacle, the mixing element means also being sized for withdrawal from the interior of the receptacle through the upright first end region after mixing of the components; and plunger means sized for insertion, after withdrawal of the mixing element means, into the interior of the receptacle through the first end region for advancement through the interior toward the second end region, to dispense the mixed components of the bone filling material through the dispenser outlet while the base means supports the first end region in the upright condition.

2. A system according to claim 1 wherein the plunger means includes means for purging air in the receptacle during advancement of the plunger means toward the second end region.

3. A system according to claim 1 further including a bone filler device, and wherein the dispenser outlet includes a fitting for dispensing the mixed components of the bone filling material into the bone filler device.

4. A system according to claim 1 further including a plurality of bone filler devices, and wherein the dispenser outlet includes a fitting for dispensing the mixed components of the bone filling material into each of the bone filler devices.

5. A system comprising:

a plurality of bone filler devices;

a receptacle for receiving components of a bone filling material in an unmixed condition, the receptacle including a first end region and a second end region oppositely spaced from the first end region; a dispenser outlet formed on the sidewall adjacent the second end region and communicating with the interior of the receptacle, the dispenser outlet including a fitting that mates with each of the plurality of bone filler devices;

base means on the second end region for supporting the first end region in an upright condition and being sized and configured for resisting tipping of the receptacle during use;

mixing element means for mixing the components of the bone filling material within the receptacle and for withdrawal from the receptacle after mixing of the components; and plunger means for dispensing the mixed components of the bone filling material through the fitting of dispenser outlet into each of the plurality of bone filler devices while the base means supports the first end region in the upright condition.

6. A system according to claim 5 wherein the plunger means includes means for purging air in the receptacle during advancement of the plunger means.

* * * * *